United States Patent
Jacobson et al.

(10) Patent No.: US 6,953,656 B2
(45) Date of Patent: Oct. 11, 2005

(54) DIRECT, EXTERNALLY IMPOSED CONTROL OF POLYPEPTIDES

(75) Inventors: Joseph M. Jacobson, Newton, MA (US); John J. Schwartz, Newtonville, MA (US); Kimberly Hamad, Cambridge, MA (US); Shuguang Zhang, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/905,831

(22) Filed: Jul. 13, 2001

(65) Prior Publication Data

US 2002/0119572 A1 Aug. 29, 2002

Related U.S. Application Data

(60) Provisional application No. 60/276,313, filed on Mar. 16, 2001, and provisional application No. 60/218,312, filed on Jul. 14, 2000.

(51) Int. Cl.[7] ............................. C12Q 1/00; C12Q 1/18
(52) U.S. Cl. ................... 435/4; 435/6; 435/7.1; 530/350; 436/501; 436/518; 204/904
(58) Field of Search ................. 435/4, 6, 7.1; 530/350; 436/518, 501

(56) References Cited

U.S. PATENT DOCUMENTS

| | | | | |
|---|---|---|---|---|
| 5,168,057 A | * | 12/1992 | Oh et al. ............... | 435/174 |
| 5,324,663 A | * | 6/1994 | Lowe ..................... | 435/320.1 |
| 5,922,537 A | * | 7/1999 | Ewart et al. ............. | 435/6 |
| 6,169,169 B1 | * | 1/2001 | Hyldig-Nielsen et al. .. | 536/22.1 |
| 6,335,201 B1 | * | 1/2002 | Allbritton et al. ......... | 436/63 |
| 6,365,362 B1 | * | 4/2002 | Terstappen et al. ....... | 435/7.23 |
| 6,379,971 B1 | * | 4/2002 | Schneider et al. ......... | 436/89 |
| 6,511,824 B1 | * | 1/2003 | Buchman et al. .......... | 435/69.1 |
| 6,689,338 B2 | * | 2/2004 | Kotov ..................... | 424/1.69 |
| 2001/0039060 A1 | * | 11/2001 | Siiman et al. ............. | 436/525 |

OTHER PUBLICATIONS

Liu et al (Bioorganic and Medicinal Chemistry Letters (1997) 7(20):2677–2680).*

Harlow et al Antibodies, A Laboratory Manual pp. 483–485 1988.*

* cited by examiner

Primary Examiner—Jeffrey Fredman

(57) ABSTRACT

Methods and compositions for rendering proteins directly responsive to an external signal utilizing modulators that themselves respond to the external signal and are associated with the proteins. In response to the external signal, the modulator alters physical properties of the specific protein molecule(s) with which it is associated, thereby altering the structural and functional properties thereof. The modulator may, for example, transfer applied energy to a protein, or to a portion of the protein, thereby changing the protein structure and function.

14 Claims, 21 Drawing Sheets

NANOELECTRODES WITH PROTEIN

RF COIL

CLOSE UP OF NANOELECTRODES

PROTEIN

ELECTRODE 1

▶ FULLY RECOVERABLE

▶ NANOCRYSTAL LINKED TO RNase ALTERS ACTIVITY IN RFMF

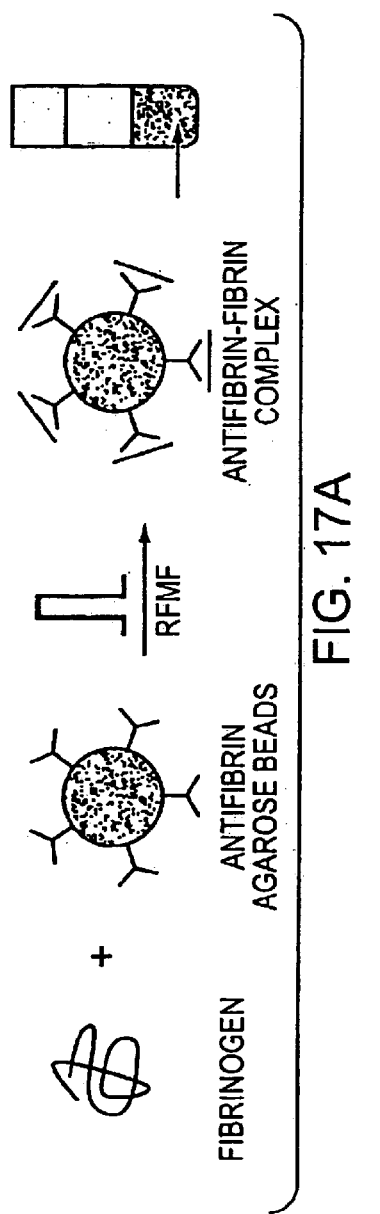
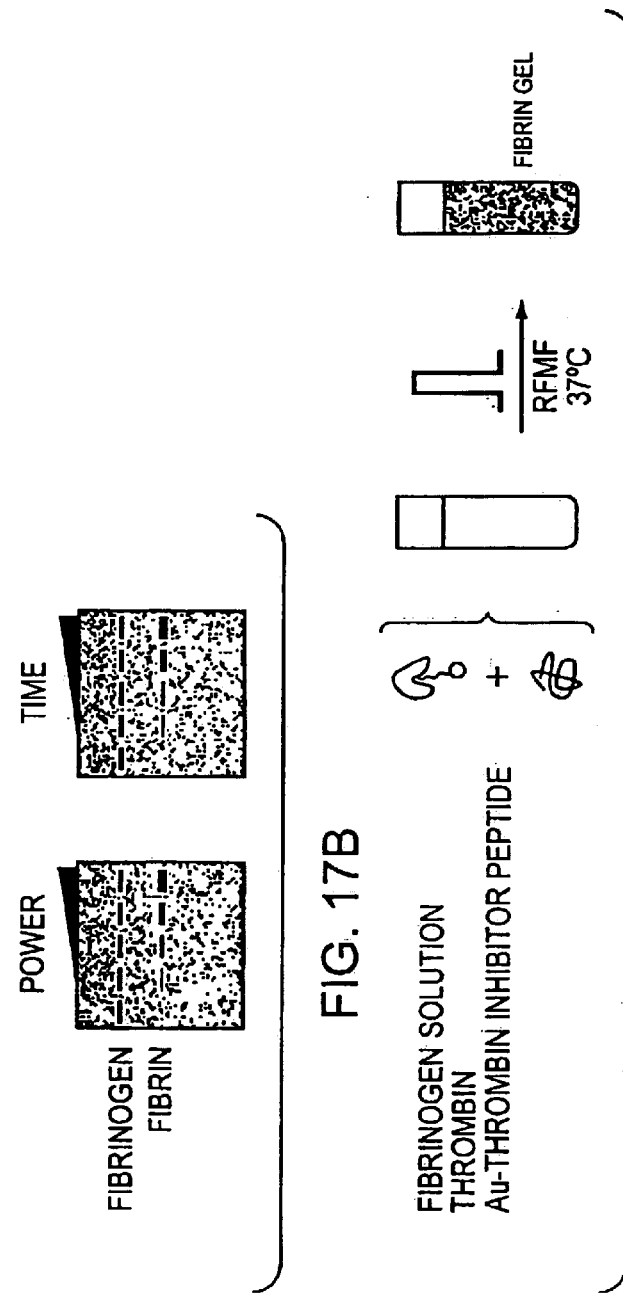
FIG. 17A
FIG. 17B
FIG. 17C

DIRECT, EXTERNALLY IMPOSED CONTROL OF POLYPEPTIDES

RELATED APPLICATIONS

This application claims priority to, and the benefit of U.S. Provisional Patent Application Ser. No. 60/276,313 filed on Mar. 16, 2001, and 60/218,312 filed on Jul. 14, 2000, the disclosures of which are incorporated by reference herein.

STATEMENT REGARDING FEDERALLY SPONSORED RESEARCH

This invention was made with U.S. government support under Grant No. DAAD16-01-C-0048, awarded by the Army. The government has certain rights in this invention.

FIELD OF THE INVENTION

The present invention relates to methods and compositions for controlling biological reactions through the use of external electric or magnetic fields or optical pulses. In particular, the invention relates to methods and compositions for controlling the structural and functional properties of proteins.

BACKGROUND

Known methods for altering the structure of a polypeptide or protein typically involve changing the physical conditions of a sample that contains the polypeptide. The sample may be heated or cooled, or the pH or salt concentration of the sample may be varied. Any one of these changes may affect the structure of a folded polypeptide. However, because they are applied globally, such changes may also affect the structures of other components of the sample. Consequently, the functional properties of all biomolecules in the sample may be affected.

Conventional techniques are also global with respect to a polypeptide molecule itself, affecting the molecule as a whole rather than a localized portion thereof. For example, the effects of a gross environmental change, such as heating, will affect the entire molecule uniformly. Even chemical reagents directed toward particular moieties will affect such moieties wherever they occur along the molecule. As a result, precise control over individual molecular entities or portions thereof has not heretofore been feasible.

Nonetheless, in many practical settings there is a need to control the function of a specific protein that is present in a heterogeneous solution containing other proteins and nucleic acids. There is also a need in the art for methods and compositions for directly or remotely altering the properties of a protein, or a portion of a protein without changing any other components of a sample containing the protein.

SUMMARY OF THE INVENTION

The invention provides methods and compositions for rendering proteins locally and directly responsive to an external signal. A protein in accordance with the invention is characterized by structural and functional properties that facilitate regulation by an external signal that does not directly affect other proteins in a sample. In addition, the signal may only affect one or more specific, localized portions of the protein. According to the invention, an external signal alters a property of a specific protein thereby changing its function. Consequently, the invention provides methods and compositions for regulating the structure and function of a protein (or portion thereof) in a biological sample, without affecting the properties of other components of the sample (or portions of the molecule remote from the affected region).

According to the invention, a modulator that is responsive to an external signal is associated with a protein. In response to the external signal, the modulator alters physical properties of the specific protein molecule(s) with which it is associated, thereby altering the structural and functional properties thereof. In a preferred embodiment, the modulator transfers applied energy to a protein, or to a portion of the protein, thereby changing the protein structure. In a particularly preferred embodiment, the modulator transfers heat to a protein or portion thereof, resulting, for example, in the destabilization of inter- or intramolecular bonds thereby causing the structure or stability of the protein to change. In an alternative embodiment of the invention, a modulator cools the protein with which it is associated, also causing a change in the structure or stability of the protein. According to one aspect of the invention, an induced structural change has a localized effect and does not alter the overall three-dimensional structure of the protein. According to another aspect of the invention, the structural change has a global effect on the protein, changing its overall three-dimensional structure. In a further aspect of the invention, the structural change alters the interaction of one polypeptide chain with another polypeptide chain. In one embodiment, this affects the interaction of one subunit of an oligomeric or multimeric protein with other subunits of the oligomer or multimer. In another embodiment, the induced structural change alters the interaction of a protein with a regulatory polypeptide or protein.

According to the invention, the modulator only directly affects the polypeptide with which it is associated, and not other components of a sample, such as other proteins or nucleic acids in a biological sample. In preferred embodiments of the invention, a modulator is covalently attached to a polypeptide. A modulator may be attached to the N-terminus, the C-terminus, or to an internal amino acid of a polypeptide chain. A modulator may be associated with a particular polypeptide region to be controlled. In one embodiment, a modulator is associated with a polypeptide in a 1:1 ratio. In one embodiment, one modulator is present for approximately every 100 amino acid residues of a polypeptide chain, and more preferably for every 50 amino acids.

In general, a modulator in accordance with the invention is active only when it is exposed to an external field, e.g., a magnetic, electric, or electromagnetic field. Preferred modulators are organic or inorganic materials that are responsive to the applied external field. Preferred modulators include metal nanoparticles, semiconducting nanoparticles, magnetic nanoparticles, and chromophores. In particularly preferred embodiments of the invention, a modulator comprises one or more of colloidal or non-colloidal gold, silicon, cadmium selenide, cadmium sulfide, indium phosphide, indium arsenide, gallium arsenide, gallium phosphide.

In some embodiments of the invention, a single type of modulator is associated with a protein. Alternatively, two or more different modulators may be associated with a single protein. The different modulators are preferably responsive to different signals. For example, two modulators may be of different types in that one is a chromophore and the other is a metal nanoparticle. Alternatively, the different modulators may be of the same type, but responsive to different signals. For example, the modulators may be different chromophores that are responsive to different wavelengths. Alternatively, the modulators may be nanoparticles of different sizes with different resonant frequencies.

A modulator may be associated with a protein by mixing a modulator preparation with a protein preparation, preferably in solution. A modulator is preferably linked to a specific protein, most preferably via a covalent bond. A modulator may be provided in a form that interacts directly with a protein to form a modified protein that is linked to the modulator. Alternatively, the modulator may be provided in a form that is incorporated into a protein during synthesis. For example, the modulator may be provided as a modified component in a chemical protein synthesis reaction. Alternatively, a modulator may be incorporated into a nascent polypeptide chain using a suppressor tRNA that is charged with a modified amino acid. In preferred embodiments, a modulator is associated with a protein in vitro. However, in alternative embodiments, a modulator is self-associated with a protein in vivo in a cell culture or in cells of an organism. Modulators of the invention are useful to remotely control reactions involving proteins. In preferred embodiments of the invention, a modulator is useful to regulate enzyme catalyzed reactions, protein oligomerization or multimerization reactions, and regulatory interactions between a protein and a regulator. According to the invention, the regulator may be another protein, a nucleic acid, hormone, or other regulatory molecule. The activity of a protein may be regulated by engineering an interaction site(s) of the protein to be quiescent until an exogenous energy pulse is applied. Once the energy pulse is applied, the protein's conformation is affected resulting in an active protein. Small molecule-protein interactions may be regulated by using a nanoparticle to specifically heat a small molecule binding point on an engineered protein.

The invention also extends to devices that are useful in exposing a protein sample to an external field. In a preferred embodiment, an apparatus of the invention includes an external field generator and a sample well that is configured to receive a protein sample to be exposed to the external field. The sample is provided in a container that is configured for the apparatus. The invention also provides a handheld device that is useful to expose a protein sample, in vitro or in vivo, to a desired external field.

Finally, the invention can be used to read out the state of a molecular system or the action of a control input into a molecular system.

BRIEF DESCRIPTION OF THE DRAWINGS

The invention description below refers to the accompanying drawings, of which:

FIG. 9($b$) shows the effect of RFMF on the activity of RNase A shown in FIG. 4($a$) as a function of time.

FIG. 10($b$) shows the effect of RFMF on the activity of RNase A in the presence of an unlinked modulator as a function of S peptide concentration (the lower panel illustrates RNase A in the presence of an unlinked modulator).

FIG. 12($b$) depicts a plot of activity as a function of recovery time. As shown in the figure, the sample recovers to 100% activity, illustrating that the Au-S18/S-peptide system is not irreversibly damaged.

FIG. 13($b$) depicts a sample that has the nanocrystal free in solution with the S18/S-peptide.

FIG. 14($b$) shows a plot of A280 as a function of reaction time. Samples that have been exposed to increasing RFMF powers have lower curves than the sample without any RFMF exposure, indicating that the activity of the Au-S18/S peptide is reduced in the presence of RFMF.

FIG. 17($a$) depicts an immunoprecipitation assay for fibrin production under RF regulation.

FIG. 17($b$) depicts a gel electrophoresis and Western blot assay system for fibrin production under RF control.

FIG. 17($c$) depicts a fibrin gelation assay.

DETAILED DESCRIPTION OF THE PREFERRED EMBODIMENTS

Figure 1:
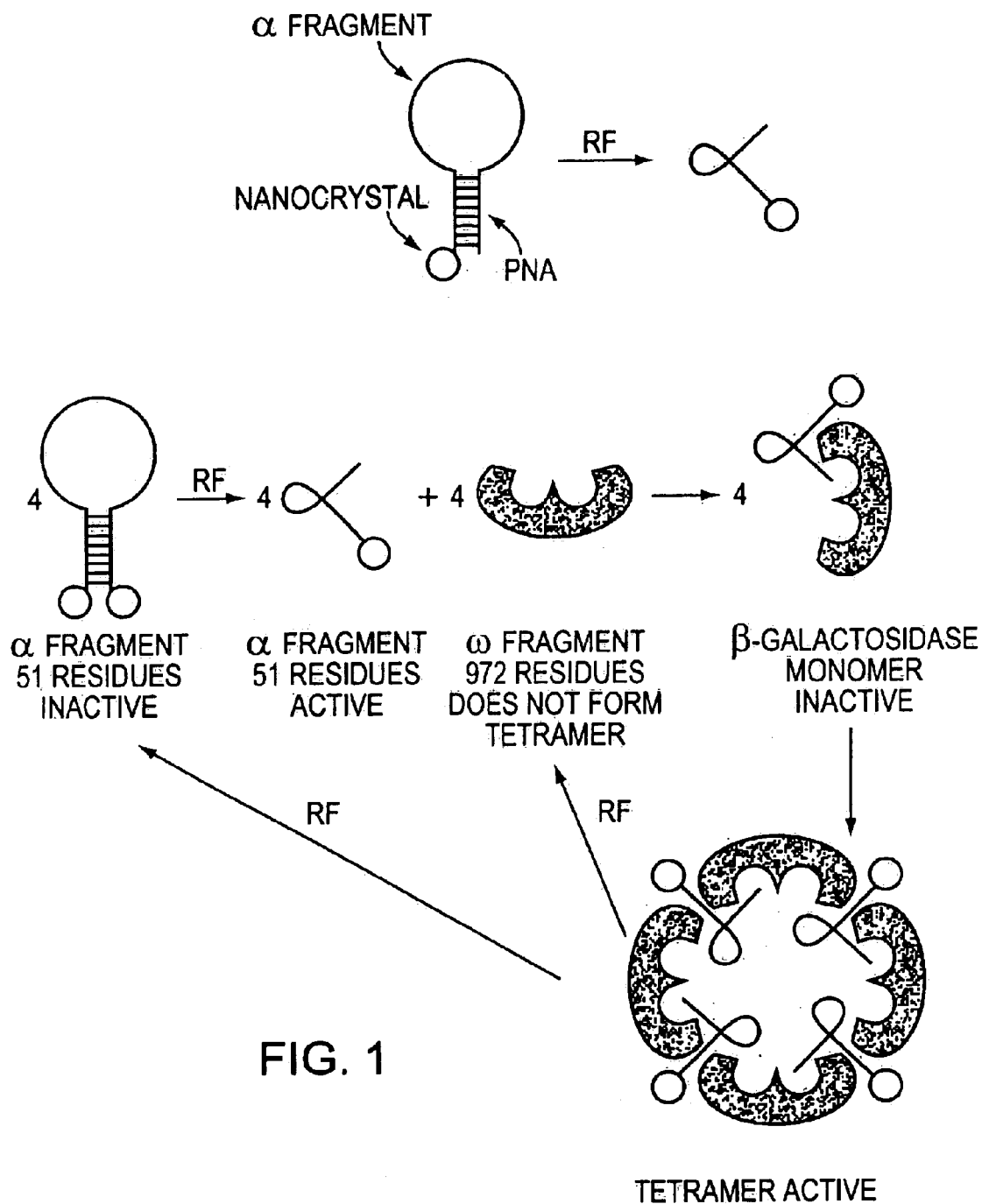
FIG. 1 is a schematic diagram showing a hybrid protein-nucleic acid structure with attached means for control and its application.

According to methods of the invention, modulators are associated with specific regions of a broad range of proteins in order to provide electronically addressable protein-modulator compositions.

1. Modulator Association a. Modulators

A modulator in accordance with the invention absorbs energy, which may be broadcast as a signal, and transfers or transduces this energy to the associated protein molecule. In one embodiment of the invention, the modulator includes or behaves like an antenna. The applied energy is generally magnetic, electric, or electromagnetic in nature, and may be, for example, a magnetic field, a radio-frequency (RF) or other broadcast signal, or optical radiation (e.g., visible, infrared, or ultraviolet light). Accordingly, a modulator is chosen for sensitivity to a preferred energy signal. Certain metals (e.g., gold, in colloidal or non-colloidal form, and ruthenium) and semiconductors (e.g., silicon, cadmium selenide) are responsive to RF and/or optical energy and, when covalently linked as nanoparticles (typically nanocrystals) to a protein, are capable of transferring applied energy to the protein molecule. For example, the excitation field may heat the particle and, consequently, its immediate environment; if sufficiently localized, the effects of the heat are confined to the protein or a portion thereof.

Chromophores integral with or constituting a nanoparticle can also be associated with a protein, transferring energy when stimulated by radiation that they absorb. Preferred chromophores respond to optical radiation in a photochemical process involving election transfer (for example the chromophore Ru(bipyridine)$_3$ which can initiate folding of cytochrome C). Magnetic materials (such as the Ferro V magnetic pigment) transduce energy when exposed to a magnetic field of sufficient intensity; for example, an alternating magnetic field will induce an alternating current in the particle, producing heat. According to the invention, other metal or magnetic materials, such as $Fe_3O_4$, $Fe_2O_3$, silver, copper, platinum, palladium can also be modulators.

It is frequently found that modulators are responsive over a range of frequencies, but provide maximal energy transduction at a single frequency or narrow range of frequencies. For example, chromophores tend to exhibit a peak absorption wavelength ($\lambda_{max}$) Similarly, nanocrystals sensitive to alternating magnetic fields may exhibit resonance behavior. This behavior may be size-dependent, with larger particles, for example, having lower resonance frequencies than smaller particles.

Modulators may be employed to reduce temperature—i.e., to withdraw energy from the immediately surrounding environment rather than to impart it. To achieve this, a magnetic nanoparticle may be attached to a protein of interest and employed in a superparamagnetic cooling arrangement. The magnetic moment of the nanoparticle is first polarized in a magnetic field and then allowed to dephase using energy contained in the protein, thus cooling the protein. In order to achieve efficient cooling, the magnetic nanoparticle should be thermally decoupled from the protein during the polarization step. This may be accomplished, for example, by initially breaking a bond between the nanoparticle and the protein (e.g., using a laser or other radiation source), subjecting the particle to magnetic polarization, and then allowing a bond to reform.

b. Methods for Associating a Modulator with a Polypeptide Chain

In general, modulators are associated with proteins covalently, e.g., through reaction with a specific reactive group on the protein or through reaction with a reactive amino acid that was selectively incorporated into the protein. For example, NHS-gold and maleamide-gold are reactive to primary amines and thiol groups, respectively. They interact with these functions and rearrange to more stable covalent bonds. In this way, the modulator may be associated with the protein at one or more predetermined sites. The ability to preferentially locate the modulator along a polypeptide chain facilitates transduction of applied energy at these sites. In some cases, it is desired to concentrate energy at these specific sites. In other cases the intention is to affect the protein as a whole, and the modulators may be spread along the length of the polypeptide chain in order to distribute applied energy throughout the molecule, or, in the case of relatively small peptides, placed only at the N-terminal or C-terminal end.

For example, sulfhydryl groups associated with protein residues react directly with colloidal gold and cadmium selenide particles and other particles including forming covalent bonds therewith. Alternatively, sulfhydryl groups form covalent bonds with nanoparticles that have appropriate functionality (e.g., maleimide) incorporated into a ligand on the surface of the particle; a suitable monomaleimido gold particle is supplied, for example, by Nanoprobes, Yaphank, N.Y. under the trade name NANOGOLD; these particles have mean diameters of 1.4 nm±10%.

Nanoparticles can also be provided with functionality (e.g., N-hydroxysuccinimidyl ester) capable of reacting with amine groups along a polypeptide chain. For example, a suitable sulfo-N-hydroxysuccinimido NANOGOLD particle is also supplied by Nanoprobes. In addition, modulators can be prepared such that they contain a functional ligand that reacts with a primary amine on the N-terminus of a protein. Other examples of amine reactive ligands are isocyanates, acyl azides, sulfonyl chlorides, epoxides, oxiranes, carbodiimides, anhydrides. Ligands that react specifically with carboxylate groups, such as the C-terminus of a protein, are diazoalkanes and diazoacetyl groups.

In one aspect of the invention, a specific part of a protein is modified to allow the addition of a non-natural ligand that is sensitive to an external signal (a modulator). Preferred methods for associating a modulator with a protein rely on enzymes which recognize specific amino acid sequences. For example, enzymes present in eukaryotic cells specifically glycosylate an asparagine-X-serine/threonine (asn-X-ser/thr) motif on a protein. A modulator of the invention can then be covalently attached to the sugar groups on the asn-X-ser motif. The glycosylation reaction can be carried out in vitro using purified glycosylation enzymes. Alternatively, the glycosylation can occur in vivo in the ER/golgi apparatus. If a cytosolic protein with the asn-X-ser motif is to be glycosylated in vivo, it can be directed to the ER/golgi apparatus by recombinantly attaching an appropriate signal sequence to its amino terminus. Alternatively, other site-specific chemical reactivities (e.g., the chemistry of a phosphorylation site) can be used to attach a modulator to a peptide or protein.

In one embodiment, a specific glycosylation motif is genetically engineered into a protein to allow site-specific glycosylation to occur. To introduce an N-linked glycosylation onto a protein, an asn-X-ser motif can be introduced into a polypeptide chain, preferably into a part of the chain that is surface-exposed when the protein is folded. As discussed above, an asn-X-ser site is uniquely modified by the natural golgi-resident enzymes in eukaryotic cells. According to methods of the invention, natural sugars or unnatural sugars can be used as specific sites for covalent addition of a modulator. Examples of covalent addition reactions are disclosed in Saxon et al., "Cell surface engineering by a modified Staudinger reaction" (2000) *Science*

287:5460 pp 2007–10 and Lemieux et al., "Chemoselective ligation reactions with proteins, oligosaccharides and cells" (1998) *Trends Biotechnol* 16:12 pp516–512. Controlled sodium periodate oxidation, or enzymatic oxidation yields sugar chains with ketone groups. These ketones react specifically with aminooxy and hydrazide compounds and accordingly can be linked to appropriately modified modulators. Alternatively a modified Staudinger reaction, between an azido sugar and a phosphine, may be used to realize carbohydrate-mediated engineered reactivity. For example, colloidal gold can be covalently linked to organic molecules through phosphine chemistry. The unique chemical reactivities of engineered positions on proteins can be used to covalently link the proteins with modulators according to the invention. Accordingly, specific, high yield, covalently bound inorganic clusters can be added to a broad range of proteins.

In another embodiment, a reactive amino acid residue can be introduced at a specific location on a polypeptide chain by expressing the polypeptide in the presence of an appropriate suppressor tRNA charged with a non-natural amino acid. Accordingly, a non-natural amino acid can be introduced into an engineered protein at one or more specific, selected positions. See, e.g., Cornish et al., "A new tool for studying protein structure and function," *Current Opinion in Structural Biology* 4:601–607 (1994); Dougherty, "unnatural amino acids as probes of protein structure and function," *Current Opinion in Chemical Biology* 4:645–652 (2000); Soth et al., "Unnatural oligomers and unnatural oligomers libraries," *Current Opinion in Chemical Biology* 1:120–129 (1997). The disclosures of these articles are hereby incorporated by reference. A modulator is then attached to the non-natural amino acid. The non-natural amino acid preferably reacts with a modulator to form a covalent bond between the modulator and the protein.

In an alternative embodiment of the invention, natural amino acids may be chemically altered to generate reactive groups that can be used to specifically add a modulator to a protein. For example, peptides that bind to inorganic crystals or even synthesize them have been isolated. See, e.g., Whaley et al., "Selection of peptides with semiconductor binding specificity for directed nanocrystal assembly," *Nature* 405:665–668 (2000); Brown et al., "A Genetic Analysis of Crystal Growth," *Journal of Molecular Biology* 299:725–735 (2000). The disclosures of these articles are hereby incorporated by reference.

In another embodiment, the sequence of a protein is altered by the addition of an engineered codon for a specific amino acid (e.g. a cysteine) or by the addition of an unnatural amino acid. Engineering a specific amino acid into a protein provides the ability to include a precisely placed chemical reactivity into a polypeptide chain. Such a reactivity can be used to interact directly with a modulator. For example, gold and cadmium selenide react covalently with the sulfhydryl group on a reduced cysteine. Accordingly, by recombinantly introducing one or more specific reactive residues into a polypeptide chain, one or more modulators can be linked specifically to the site(s) of the engineered residue(s).

In an alternative aspect of the invention, a polypeptide may be synthesized chemically. The wholesale chemical synthesis of a polypeptide allows a reactive amino acid to be directly incorporated into a chosen site on the polypeptide chain. In a preferred embodiment, a protein nucleic acid (PNA) moiety is included into the polypeptide chain. This is possible, since the backbone of PNA and peptides are chemically complementary. A synthetic polypeptide-PNA molecule can be hybridized to a complementary nucleic acid or PNA, or to another polypeptide comprising a complementary PNA. Any one of these complementary molecules can be associated with a modulator. Accordingly, a synthetic polypeptide-PNA molecule can be associated with a modulator via a hybridization reaction. Modulator-PNAs may be used as hybridization effectors, which can be melted by an external energy source according to methods of the invention. This synthetic method offers the ability to engineer specific hybridization/interactions between proteins, or internally within a protein, and to allow a modulator to be associated with these proteins. In a preferred embodiment, the strength of the hybridization is adjusted to accommodate the steady state accumulation of desired peptide structures (e.g., if the hybridization is too strong it may inhibit the peptide's desired activity or conformation).

In a further aspect of the invention, a portion of a natural protein can act as a modulator in vivo. For example, a chelating protein such as a phytochelatin or a polycationic peptide assembles inorganic nanocrystals from solution. Alternatively a protein that has a native conductivity, such as a carotein, may be used in methods of the invention. In one embodiment, a portion of a protein that can act as a modulator in vivo is associated with a protein in order to directly regulate its function. The protein moieties also may be associated recombinantly, or via protein-protein interactions (e.g. via PDZ domains, SH3/SH2 or antibody antigen or other protein-protein interaction).

Modulators can be associated with monoclonal antibodies that are reactive to an epitope tag sequence (e.g. MYC, His(6), HA). These antibodies are commercially available from several sources and the short epitope may be included in an engineered cDNA at almost any surface-exposed position. Alternatively, non-covalent association of a modulator labeled peptide with a target protein may be used as a targeting technique (for example, the S-peptide and S protein fragments of RNAase A shown in Examples 1–2).

In another aspect of the invention, an antibody or an antibody fragment is linked to a modulator, and the resulting immuno-modulator binds to a specific epitope on a protein, thereby associating the modulator with the protein (see above).

c. Considerations for Protein Modification

According to the invention, selective incorporation of a modulator within a protein is achieved by associating complementary chemical functionality with one or more specific amino acid residues, so that only these residues react with the modulator. For example, an amine- or sulfhydryl-reactive amino acid may be incorporated within the polypeptide backbone by any of various techniques as discussed above. However, an important consideration when choosing a site for the incorporation of a modulator into a protein is the three-dimensional conformation of the protein. Indeed, the structural and functional properties of a protein are tightly linked, and the addition of a modulator moiety to a random location on the protein could disrupt the natural properties of the protein.

According to the invention, a modulator is preferably associated with a protein at a location that preserves the natural function of the protein, and allows the natural function of the protein to be regulated by activation of the modulator. In order to select a position for attaching a modulator to a protein, the following considerations are useful. Information about the structure of a protein (derived from a crystal structure or an NMR structure, or computationally as described, for example, in U.S. Pat. No. 5,424,963) is useful to identify a naturally reactive site, or to select a position at which to introduce a reactive site, that would preserve the function of the protein while allowing the protein activity to be regulated by a modulator attached to the reactive site. In addition, information about surface-exposed residues and/or structurally and functionally important residues is useful to choose a site for the addition of a modulator. Surface-exposed amino acids are preferred for the sites of nanocrystal attachment. These sites are accessible to site-specific reactive chemistries, whereas buried reactive sites are inaccessible. In a preferred embodiment, a cysteine is engineered into a surface accessible site. Cysteines are relatively rare amino acids with a unique chemical reactivity (SH), and placement of a cysteine in a surface-exposed region allows for the site-selective reaction with a modulator such as a maleimide-linked nanoparticle.

In general, a modulator is linked to an area of a protein that will not alter the protein activity substantially. For example, a modulator is preferably linked to a region that is relatively floppy (e.g., a region that does not have specific stabilizing interactions with the rest of the protein). However, the modulator is preferably placed close enough to an amino acid that is essential for the function of the protein so that an external energy pulse (electric, magnetic, or photon) alters the protein's structure and/or function. Preferred sites for modulator attachment can be chosen using data from crystal structures, optical/electronic/NMR spectroscopy, empirical genetic screens, allele and species sequence comparisons, and computer based structural prediction algorithms.

In one embodiment of the invention, a modulator is associated with the active site of a protein in order to directly affect the functional properties of the protein. According to the invention, a preferred distance between the modulator and the active site is determined by several factors including the sensitivity of the active site to a change in conformation, the energy field used to activate the modulator, and the energy transferred from the modulator to the protein. In one set of embodiments, a modulator is located near an active site residue on the polypeptide chain. The optimal proximity of the modulator to the active site residue may be determined based on diffusion rates of heat. The induction heating of the modulator produces a temperature gradient between the modulator and the active site residue. The dissipation of heat is dependent on the time, heat capacity of the protein and the solvent. In some embodiments of the invention, heat dissipation may be faster than 100 picoseconds. In alternative embodiments, a modulator is located at a site that is distant from an active site residue on the polypeptide chain, but close to the active site in the folded protein. Again, preferred locations on the polypeptide chain can be determined based on heat diffusion rates.

2. Applications

In one embodiment of the invention, a modulator is dispersed in a protein solution and excitation of the modulator causes the temperature of the entire solution to change. However, in this embodiment, the effect of the modulator is not limited to a specific protein or portion thereof. Therefore, preferred methods of the invention involve associating a modulator with a specific protein or a specific portion of a protein in order to directly control only that protein or portion thereof.

According to the invention, a protein with an associated modulator may be transitioned from an active state to an inactive state by exposing the modulator to an appropriate external control field. As will be discussed in more detail below, direct control of a binding protein provides a method for controlling whether a ligand is bound or released from the binding protein. Similarly, direct control of an enzyme provides a method for controlling the amount of enzyme product produced by the enzyme reaction. Accordingly, an enzyme pathway may be controlled by controlling one of the enzymes in the pathway. Such control is particularly effective if the activity of the enzyme is rate limiting to the pathway.

a. Direct Control of Protein Structure and Function

In one application, a modulator facilitates on-demand denaturation or unfolding of a protein or portion thereof. When subject to, for example, optical or RF radiation, the modulator-containing polypeptide is heated, causing non-covalent bonds to be broken, but the surrounding environment (including proteins lacking modulators) is substantially unaffected.

The effect of a nanoparticle on protein stability is demonstrated in Example 2. This non-limiting examples show that induction heating of a nanocrystal can unfold proteins or portions thereof. Induced unfolding typically occurs on a time scale on the order of seconds to milliseconds. The unfolding of a portion of a protein generally decreases the overall stability of the folded protein. However, induction heating is localized and can be used to unfold portions of a protein selectively by, for example, breaking selective non-covalent bonds.

Selective disruption of non-covalent bonds in a protein can be employed to numerous ends. In one implementation, a modulator is associated with an enzyme in order to control enzyme activity. Preferred enzymes include, kinases, proteases, DNA polymerases, RNA polymerases, dehydratases, oxidoreductases, nucleases, lyases, ligases, synthetases, ribosomes, ATP synthases, RNA ribozymes telomerases, hydrolases, glycosidases, isomerases, dehydrogenases, protein kinases, phosphatases, transposases, oxidases, reductases, splicesomes, chaperonins, transferases, deaminases, ATPases. The enzyme may be a monomeric enzyme. Alternatively, the enzyme may be multimeric. According to the invention, a multimeric enzyme may be controlled by controlling a single subunit of the enzyme. This is true whether the enzyme is a homomultimer (such as a homodimer, or higher order homomultimer), or a heteromultimer (such as a heterodimer or higher order heteromultimer) including large multienzyme complexes such as a proteosome. Other preferred multienzyme complexes include polyketide synthases, ribosomes, G coupled protein receptors, and flagellar ATP synthases. Control of a multienzyme complex is preferably accomplished by associating a modulator with a regulatory subunit of the enzyme complex. According to the invention, transduction of energy into the molecule through activation of the modulator may be found to enhance or inhibit enzymatic activity, depending on the context.

In another application, a modulator is associated with a structural protein. Preferred structural proteins include collagens, actins, myosins, tubulins, histones/nucleosomes, keratins, neurofilaments, dentin and other matrix proteins. In a preferred embodiment, a modulator is associated with a polymer of structural proteins. One or more modulators may be associated with each protein monomer in the polymer. However, a modulator can control the polymerization of structural protein monomers even if only a subset of the monomers is associated with a modulator. For example, if approximately 10% of the monomers are associated with a modulator, exposure of the polymer to an external field causes the polymer to depolymerize at approximately every tenth subunit of the polymer. This limited depolymerization is sufficient to alter the structural properties of the polymer. According to the invention, destabilization of a structural protein polymer is useful to control a biological event that relies on a stable polymer. For example, modulators can be used to control biological events such as cellular motility or stages of the cell cycle involving cell division or chromosome migration.

In one aspect of the invention, a modulator induced change is irreversible. Accordingly, when a modulator associated protein is exposed to an appropriate external field, the protein takes on a new and stable conformation due to energy transfer from the modulator. When the external field is removed, the protein remains in the new conformation. According to this aspect of the invention, a single pulse of energy is sufficient to induce a permanent protein conformational change.

In another aspect of the invention, a modulator-induced change is reversible. Accordingly, when a modulator-associated protein is exposed to an appropriate external field, the protein takes on a new conformation only for as long as the external field is present. When the external field is removed, the protein returns to its original conformation. According to this aspect of the invention, a single pulse of energy induces a temporary conformational change in a protein. The modulator induction can be used to control a protein in a switch-like manner. Accordingly, a biomolecular switch can be produced in solution.

A modulator may be used in connection with a hybrid protein-nucleic acid system to control protein function (FIG. 1). For example the nucleic acid part of such a system, to which a modulator is attached, may be self hybridizing thereby rendering the protein part inactive in the absence of an RF field. Upon application of an RF pulse the nucleic acid portions of the system dehybridize, releasing the active protein parts. Such a system is illustrated by the non-limiting example shown in FIG. 1. In this example, the system has a self-complementary pair of PNAs with nanogold particles linked to the alpha fragment of β-galactosidase. The omega fragment of β-galactosidase requires the presence of the alpha fragment to assemble into an active tetrameric molecule. In the absence of an external field, the PNAs form complementary pairs, thereby rendering the alpha fragments inactive and unable to interact and assemble with the omega fragments. When an external field is applied, the PNAs disassociate from each other thereby freeing the alpha fragments to interact with the omega fragments and form active tetramers. It is important that the strength of the PNA interaction be optimized. If the interaction is excessively strong, inactive hybridized alpha fragments will reform after an external field pulse, as opposed to the active tetramers. In contrast, if the PNA interaction affinity is insufficient, the inactive hybridized alpha fragments are not formed. Achieving the optimal PNA interaction strength is straightforward and does not require undue experimentation. Those skilled in the art can, for example, vary the length of the nucleic acid chains to obtain the proper degree of interaction.

Radio frequency biology, like molecular biology a few years ago, represents a new dimension of biology. Virtually all biological molecules can be linked with gold or other semi-conducting nanoparticles and subjected to remote electronic controls. Such well-controlled systems will have profound implications in finely dissecting detailed molecular interactions and complex formations. A broad range of applications relating to radio-frequency biology can be anticipated. For example, the processing rate and fidelity of DNA and RNA polymerases can be precisely regulated; complex formations and interactions of protease and protease inhibitors can be well controlled. The catalytic activities and the rates of catalysis of a variety of enzymes including ribozymes can be fine tuned and switched on and off electronically and remotely. The membrane receptors and ligand interactions can be finely controlled for their intimate and flexible complex formations. The membrane transporters can be well-executed to govern protein and nucleic acid translocations. The ion channels can be opened and closed at will and at various time points. The proton pumps can be regulated for energy production. The neural transmitters can be precisely regulated for their timely release. Finally, dimerization, oligomerization, and the complex assemblies of ribosomes, splicesomes, chaperones and proteosomes may also be organized.

Radio frequency biology provides extraordinary tools and unprecedented control precision to study molecules and their interactions. These new tools and technologies will undoubtedly accelerate and advance knowledge in this field in finest detail. It not only opens new avenues for asking important questions but also to attain the ultimate answers in biology.

One aspect of the present invention pertains to achieving reversibility of protein conformation. Certain classes of proteins can exist in multiple conformations depending on their energy states. For instance, a protein may exist in a first conformation if it is heated slowly for a period of time and then quenched rapidly. Alternatively, it may exist in a second conformation if it is heated slowly and subsequently cooled slowly. By attaching a modulator to such a protein, a predetermined sequence of RF pulses may be used to cause the protein to adopt either the first or the second conformation, depending on the sequence of RF pulses. As an example, a rapid RF pulse may be applied to cause the inactive form of β-galactosidase to shift to the active form. A preferred RF pulse (or series of pulses) provides sufficient energy for the modulator to alter the protein without changing its surroundings. If the modulator works by heating, the timescale for heating the surroundings can be calculated from the diffusion of heat into the surroundings, which depends on the heat capacity of the protein and the solute. Therefore, a preferred pulse (or series of pulses) heats the desired part of the protein, but not its surroundings. In many embodiments, preferred pulses are on the order of microseconds to seconds. To induce a change in a protein from an active form to an inactive form, a slow RF pulse, preferably one on the order of minutes to hours may be applied. This illustrates a general principle according to which certain proteins, nucleic acids or hybrid complexes stably exist in multiple states depending upon the state of the energy applied to them.

Figure 2:
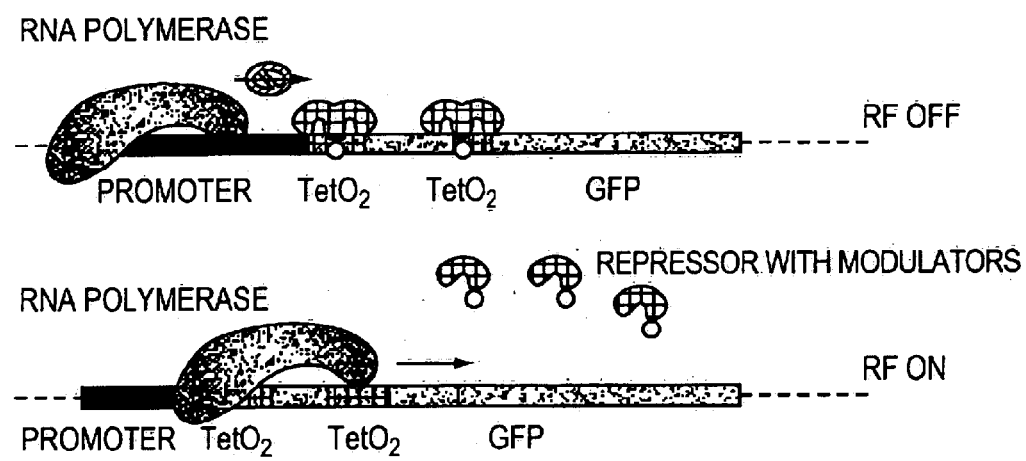
FIG. 2 is a schematic diagram showing external control of the expression of a gene.

In accordance with the present invention, a modulator may also be used to control gene expression by directly controlling the binding of a protein to a gene operator. The system shown in FIG. 2 illustrates this principle. FIG. 2 shows a system for electronically controlling Green Fluorescent Protein (GFP) expression using a molecularly modified Tet repressor. The modified Tet repressor comprises a modulator according to the invention. A modulator is added directly to the disordered loop at the head of alpha helices 1 and/or 3 of the Tet transactivator. In the unstimulated (RF off) state the Tet repressor protein forms dimers and binds to the Tet operator, preventing transcription by RNA polymerase. In the stimulated (RF on) state, the Tet repressor is conformationally altered and falls off the DNA operator sequence Tet $O_2$, allowing transcription to proceed.

Figure 3:
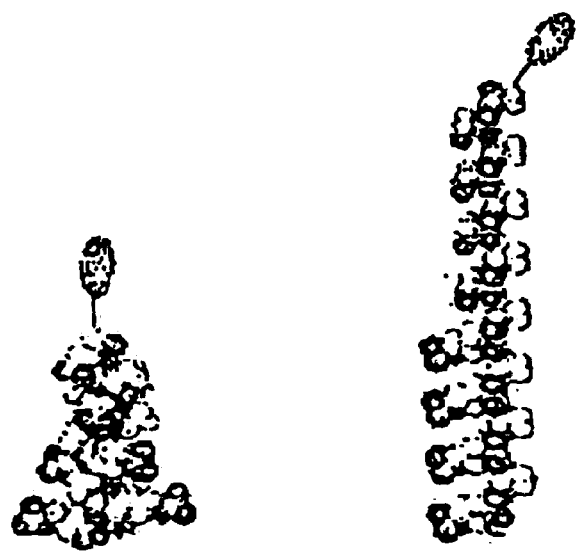
FIG. 3 is a schematic diagram of amino acid sequences with attached means for control in which such sequences are designed to have either appreciable conformational changes for the purposes of actuation or in which the conformation of the amino acid sequence is dependent on the time energy history of energy injected into the system.

Another application of the invention is a directly activated peptide actuator. FIG. 3 shows an example of an RF activated peptide actuator. According to the invention, a class of dipolar peptides undergo a dramatic and reversible structural transition between a beta-sheet conformation and an alpha helical conformation in response to a change in temperature. Short repeating units of peptides have been found to undergo very abrupt alpha-helix to beta-sheet transitions that can be induced by temperature or pH change. Because of the differences in the conformation between the two structures, the overall length change is quite dramatic. According to the invention, this structural change can be directly controlled by associating the peptide with a modulator. As shown in FIG. 3, when such a peptide is in the beta-sheet form, the peptide amide backbone is extended 3.4 Å per residue with a total length of approximately 5 nm. In contrast, in the alpha helical form, the backbone is coiled like a spring and extends 1.5 Å per residue with a total length of approximately 2.3 nm. According to the invention, an electronic molecular switch based on such a peptide is prepared by incorporating into the peptide a specific reactive center amenable to linkage (i.e. a thiol group). A modulator may be covalently bound to form a nanostructure handle, preferably of approximately 1 nm in size. The preferred size is a function of the size of the modulator relative to the peptide. Larger modulators are bulky and may inhibit peptide functionality. In extreme cases where the modulator is very large (on the order of microns), peptide solubility may be compromised and the peptide-modulator complexes may be difficult to manipulate in solution. An RF pulse tuned to the resonance of the modulator to induce a local perturbation of the peptide structure can be used to transition the peptide from an alpha to beta sheet conformation. Typically, when the peptide cools down, it returns to an alpha-helical conformation.

Figure 4:
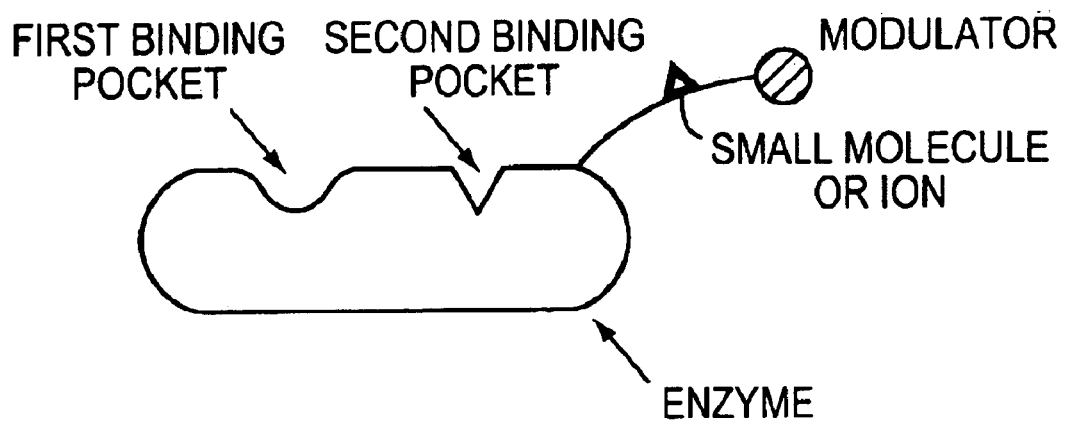
FIG. 4 is a schematic view of another approach to controlling an enzyme system.

Methods of the invention can also be used to control an enzyme with multiple binding pockets in which the presence of an ion or molecule in a second binding pocket affects the binding affinity of a first pocket (FIG. 4). By attaching a modulator in proximity to the second binding pocket one may control the binding to the pocket and thus the affinity of the first pocket. Such a system forms a type of AND gate in which a binding event at the first pocket only occurs if both the RF field is off, allowing binding to take place to the second pocket, and the necessary small molecule or ion which needs to bind to the second pocket is present in solution. An example of such a system is the $Mg^{2+}$ binding pocket in a DNA polymerase enzyme or in reverse transcriptase. The polymerase enzyme will not progress along its template without $Mg^{2+}$ binding. Thus by controlling the binding of $Mg^{2+}$ to its binding pocket on the polymerase enzyme, methods of the invention can be used to turn on and off the polymerase enzyme.

Figure 5:
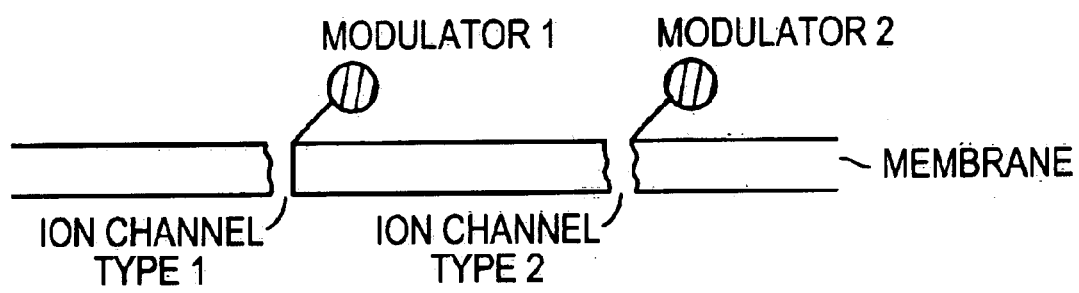
FIG. 5 is a schematic view of a system for direct electronic control of ion channels.

In another aspect of the invention, a modulator is used to control ion flow across a membrane (such as with G-proteins, membrane ion channels, NMDA and other neurotransmitter receptors) (FIG. 5). Different types of ion channels in a membrane are preferably associated with different types of modulators that are responsive to different external signals. In one embodiment, a modulator distorts a normal ion channel into a nonfunctional form upon the application of an external energy field. In another embodiment, a modulator distorts a mutated ion channel into a functional form upon application of an external energy field. Accordingly, the permeability of the membrane to different ions can be directly regulated. In a preferred embodiment, a modulator is attached to a region of an ion channel which can "gate" the activity of the ion channel. Typically, "gate" regions coincide with flexible regions near the mouth and central portions of the internal side of an ion channel. Alternatively, a nanoparticle is placed onto a channel that can exert force on these sites thereby regulating their activity.

Figure 6:
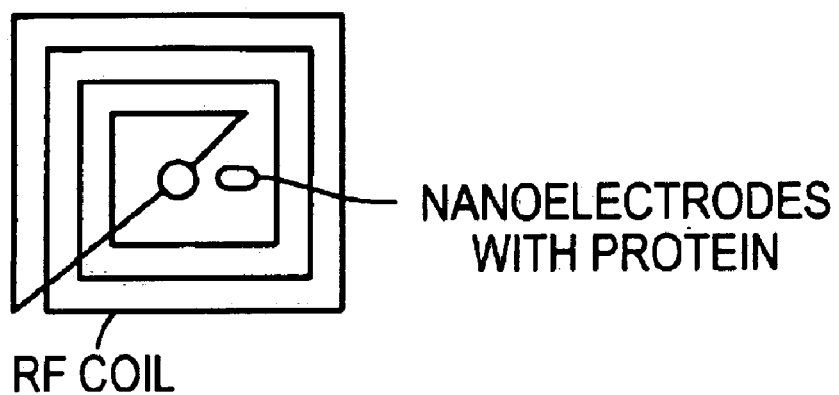
FIG. 6 is a schematic view of a hybrid protein-resonator system for remote detection of protein-binding events.
Figure 6:
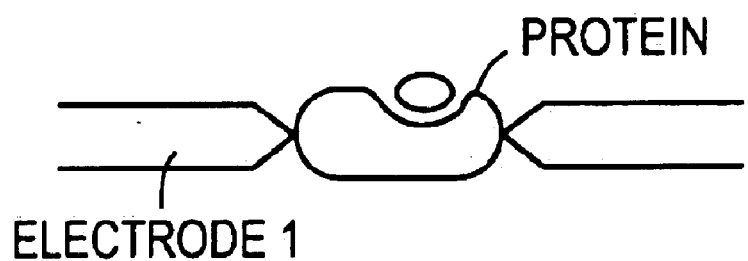

In another embodiment of the invention, a protein has appended to it a synthetic resonator (FIG. 6). The RF resonance of the resonator changes depending upon the presence of a molecule in the protein's active site. This is similar to an RF single electronic transistor or an RFID tag.

b. Considerations for Transferring Energy to Proteins

The ratio of modulator to amino acid residues in a protein that is required to reliably induce the unfolding of the protein or a portion of the protein depends on several factors. These include the nature of the modulator, the transduction efficiency of the modulator-protein system, the intensity of the applied field and the natural stability of the protein.

Preferably, the energy imparted to a protein-modulator composition of the invention is not sufficient to break a covalent bond, e.g., less than 2 kcal/mole. However, the appropriate amount of energy to be transferred to a protein depends on the amount of energy needed to obtain the desired conformational change and can be straightforwardly optimized without undue experimentation. For example, if the energy the modulator is transferring to the protein is heat, different proteins will unfold their active site at different temperatures. The amount of energy needed to cause unfolding can be determined experimentally. Techniques such as circular dichroism (CD) spectroscopy can provide information on the structure of a protein as it is altered by a modulator transferring energy to it. In addition, the amount of energy required to obtain a desired change in the protein may be altered by changing the physical properties of the solution the protein is in (e.g., the temperature, salt concentration, or pH of the solution).

Once the desired amount of energy to be transferred to a protein is determined, an appropriate protein-modulator composition is produced by selecting the type of modulator, the number of modulators, the location of modulator attachment, and the strength of the external field.

Different types of modulators transfer different amounts of energy. For example, a 10 nm gold particle provides more energy than a 2 nm gold particle. Different modulators with different excitation characteristics can be used on the same molecule or on different molecules. Thus, chromophores each having a different $\lambda_{max}$ can be attached to the same protein. Their selective activation, through application of radiation at one or more of the $\lambda_{max}$ wavelengths can be used to impart different amounts of energy to the protein. The same effect may be produced using metal, semiconductive or magnetic nanocrystals having different resonance frequencies. The number of modulators attached to a protein also affects the total amount of energy transferred to the protein when exposed to an appropriate external field.

The location of a modulator along a polypeptide chain is also important. The degree of importance depends, in part, on the extent to which energy from the modulator is transferred along the chain. The extent to which energy from the modulator is transferred to residues that are distant on the peptide chain, but close in the three-dimensional structure of the protein is also important.

By locating differentially responsive modulators at various spaced-apart points along the length of a protein molecule and selectively activating them, selective activation or inactivation of specific protein regions can be achieved.

In addition, for a given modulator-protein composition, the amount of energy transferred to the protein from the modulator can be varied by varying the time of exposure to an external field (e.g. by varying the time of an RF pulse, or the number of RF pulses). Alternatively, by using a suboptimal external field (e.g., a wavelength different from the $\lambda_{max}$ wavelength) the amount of energy transferred from the modulator to the protein can be reduced.

3. Readout

Figure 7:
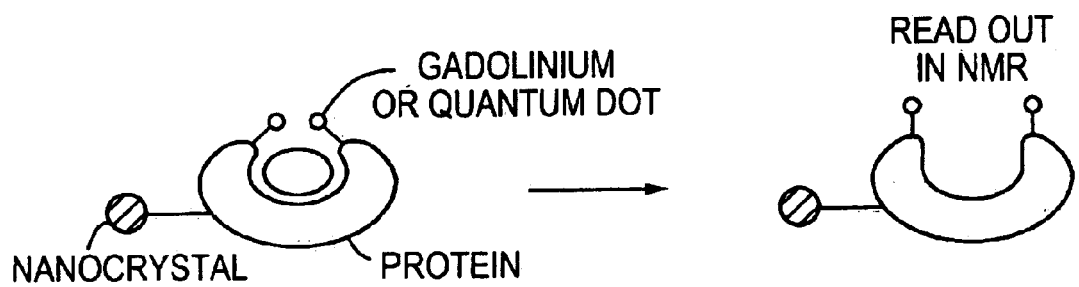
FIG. 7 is a schematic view of a system for reading out the state of a molecular system or the action of a control input into a molecular system by the means of nuclear magnetic resonance.

The invention can be used to detect—i.e., "read out"—the state of a molecular system or the action of a control input into a molecular system. This may be accomplished optically, by means of nuclear magnetic resonance, or through direct electronic means. FIG. 7 shows the use of NMR to detect protein activity. The protein is decorated with Gd or other NMR-active atoms at specific sites. The protein in its active state undergoes a conformational change, which detectably changes the magnetic resonance between the two Gd atoms. Alternatively, NMR-active atoms may be replaced with quantum dots, which change optically depending on their proximity to each other. Such conformational changes may come about from a binding event, a change in the environment (chemical, optical or temperature) or through introduction of energy coupled into a modulator.

With reference to the structure shown in FIG. 7, the readout-facilitating entity may be quantum dots which are either quenched by a quencher or which change their fluorescent properties depending on the presence or absence of a bound molecule. A gold nanoparticle, for example, may be used as a quencher. Subjecting structures that contain a conducting nanoparticle to an AC magnetic field induces an eddy current in such nanoparticles. This eddy current, in turn, generates its own highly localized magnetic field, which may be used to increase the NMR signature from a nearby NMR-active atom (such as Gd) or from another molecule. The effect may be further enhanced by incorporating a nano-ring in place of a nanoparticle. This is similar to a focusing coil used in MRI but at a vastly reduced length scale.

In some of these schemes for readout, it may be difficult or impossible to read from a single molecule. An important general approach enabled by modulators is the ability to synchronize the output from many biomolecules simultaneously so that their collective output may be detected. This may facilitate, for example, determination of the concentration of a particular species. Thus, antibodies to that species may include appended modulators that facilitate detection. The incident RF power may be controlled to keep each antibody in a nonfunctional form; cessation of RF power effectively resets the measurement time frame and places each antibody in its functional form, allowing binding now to take place. Readout may be accomplished, for instance, as shown in FIG. 7.

Figure 8:
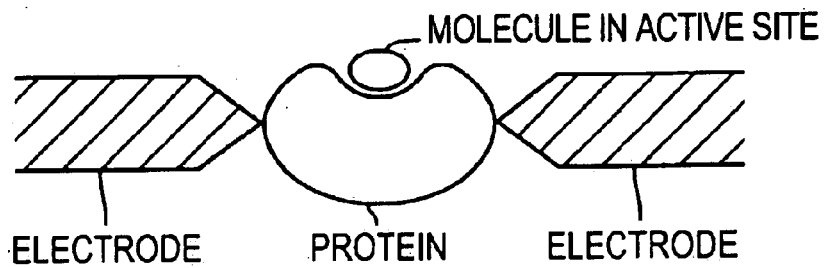
FIG. 8 shows a schematic view of a system for direct electronic readout of the state of a molecular system or the action of a control input into a molecular system.

A protein in an active state has a different electrical conductivity than its inactive state. FIG. 8 illustrates the use of electrical conductivity of a protein to determine whether or not the protein is active or inactive.

A final example involves reading out multiple channels of information. In a representative approach a number of Gd atoms in a cage are attached to an antibody of interest in proximity to the antibody's binding site. Such cages further have attached to them independently addressable modulators. In the closed state, such cages present a symmetric environment to the Gd atom, resulting in a reduced or negligible NMR signal. After modulation, however, the cages are opened, breaking the symmetry and exposing the Gd atom to the contents of the antibody binding site (if present). In this way, the contents of a number of different binding sites on different antibodies may be read out at different times.

4. Cooling

The mean molecular temperature of a biomolecule may be lowered (rather than increased) relative to its surroundings by attaching a magnetic nanoparticle to the biomolecule of interest, such as a nucleic acid. Such a magnetic particle may be used in a superparamagnetic cooling arrangement in which the magnetic moment of the nanoparticle is first polarized in a magnetic field and then allowed to dephase using energy contained in the biomolecule, thus cooling the biomolecule. In order to achieve efficient cooling the magnetic nanoparticle should be thermally decoupled from the biomolecule during the polarization step. This may be accomplished by initially breaking a bond between the magnetic nanoparticle and the biomolecule with a laser or other means, then facilitating magnetic polarization, which allows the bond to reform.

The invention is further illustrated by the following non-limiting examples.

EXAMPLES

Example 1

Methods and Compositions for Associating Modulators with Proteins

Ribonuclease S was associated with a modulator, such as a gold nanocrystal according to the following non-limiting method. A portion of the protein Ribonuclease S, the S-peptide, was synthesized so that it contains a cysteine residue and a spacer of two extra amino acids (glycines). The cysteine residue was on the N-terminus of the S-peptide. The modulator to be associated with the S-peptide was a gold nanocrystal that is 1.4 nm in diameter and is soluble in the solvents in which the Ribonuclease S is functional (for example phosphate buffer solution, which contains 13.7 mM NaCl, 2.7 mM KCl, 4.3 mM $NaH_2PO_4$, 1.4 mM $KH_2PO_4$). The modulator had a ligand maleimide group on its surface that can react with the cysteine residue on the S-peptide. The modulator was incubated with the S-peptide to permit the reaction of the maleimide with the cysteine, resulting in a covalent linkage between the two. The modulator-S-peptide complex was then incubated with the rest of the Ribonuclease S complex, the S-protein. This allowed the modulator-S-peptide complex to associate with the S-protein, forming a noncovalently bonded complex. The resulting system was a fully functional Ribonuclease S that is associated with a gold nanocrystal in one section.

Example 2

Direct Inductive Heating of a Protein Associated with a Modulator in Solution

Figure 9A:
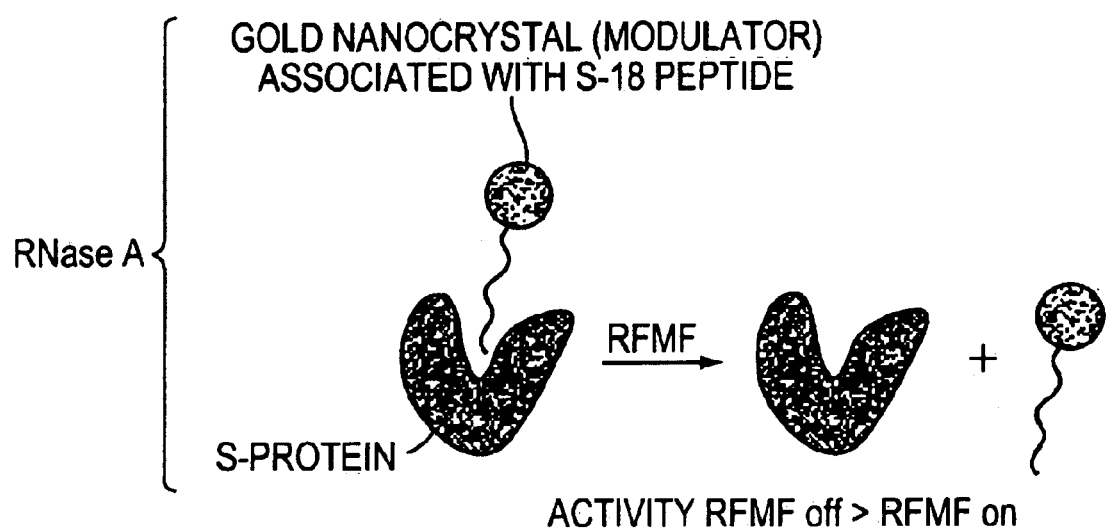
FIG. 9($a$) illustrates the effect of RFMF on RNase A with a modulator linked to the S peptide.
Figure 9B:
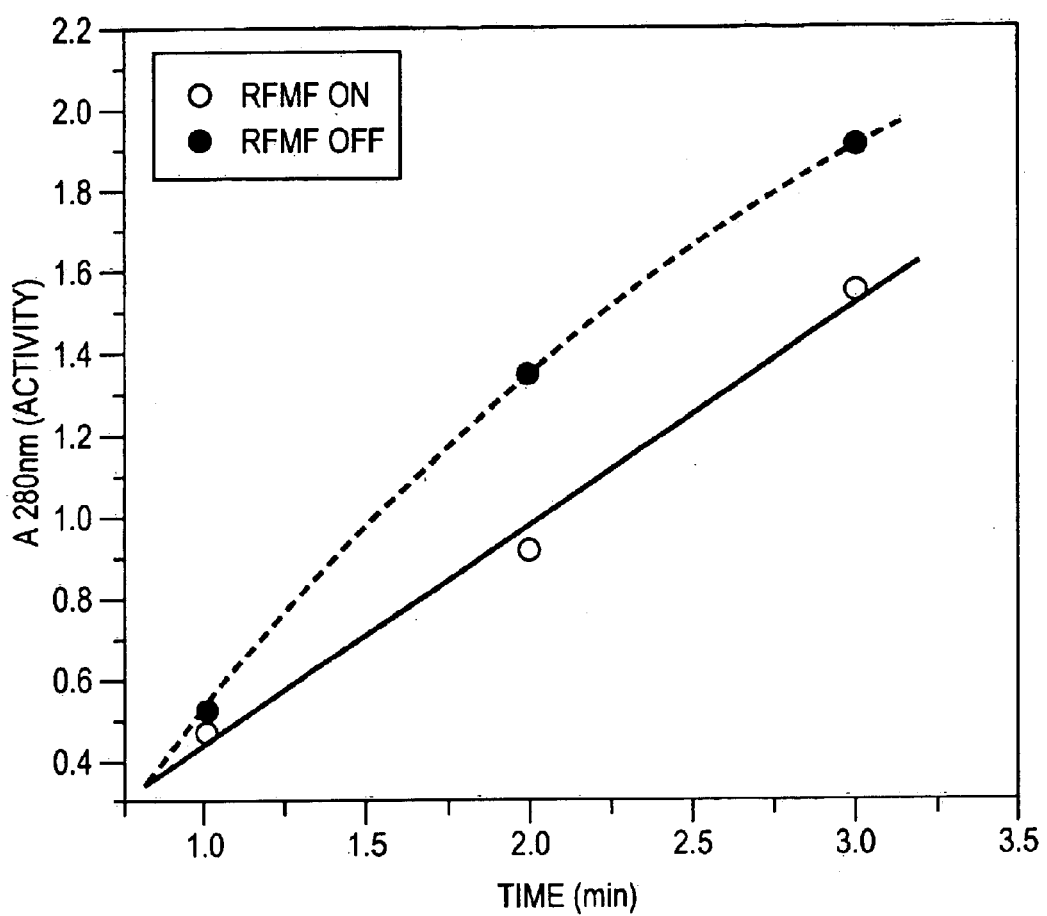
Figure 10A:
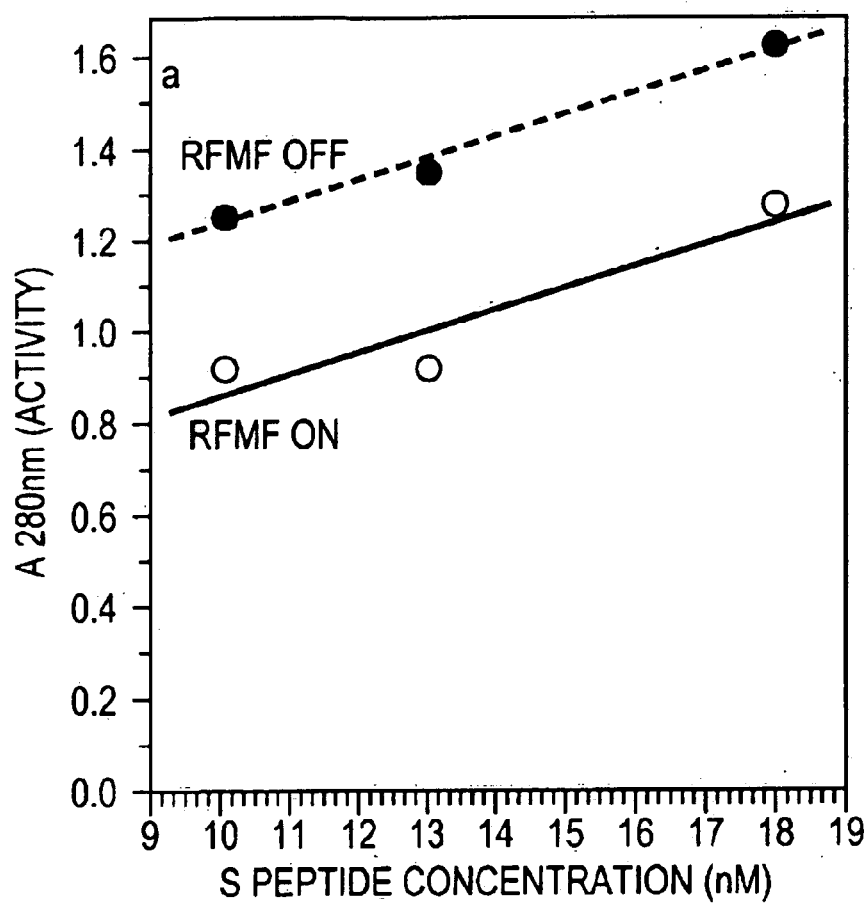
FIG. 10($a$) shows the effect of RFMF on the activity of RNase A linked to a modulator as a function of S peptide concentration (the lower panel illustrates the modulator linked to the S peptide of RNase A).
Figure 10A:
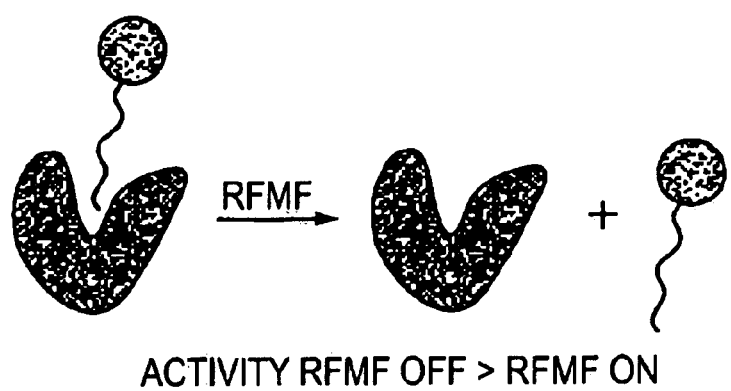
Figure 10B:
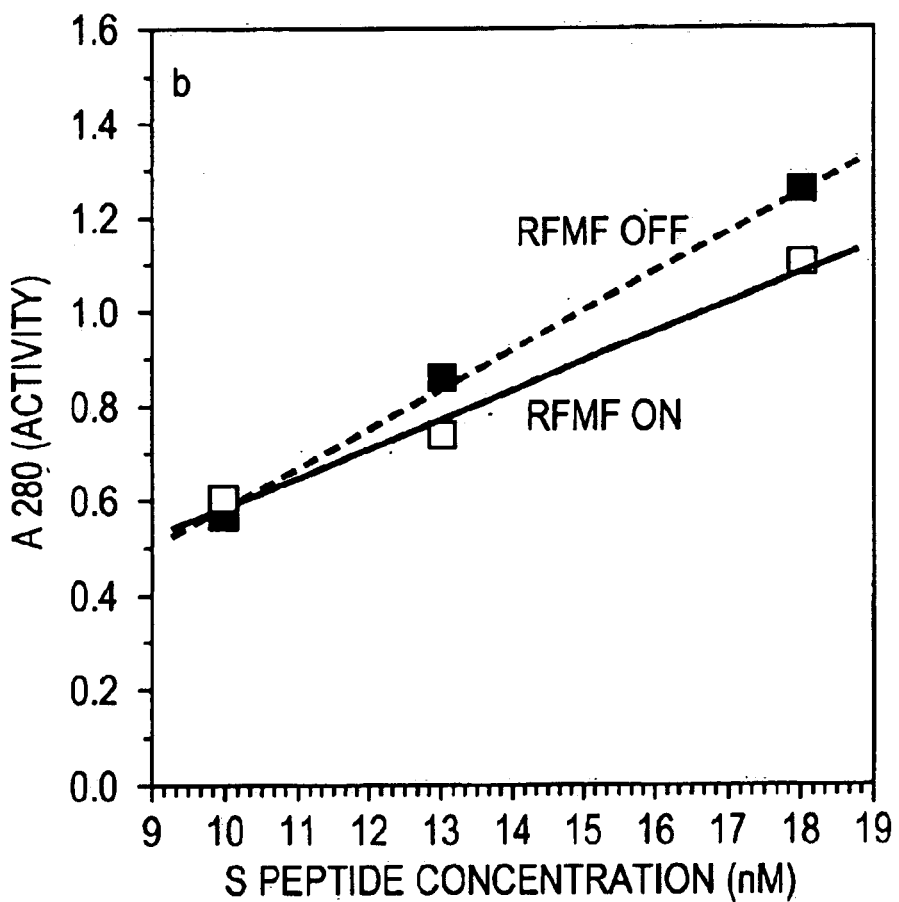
Figure 10B:
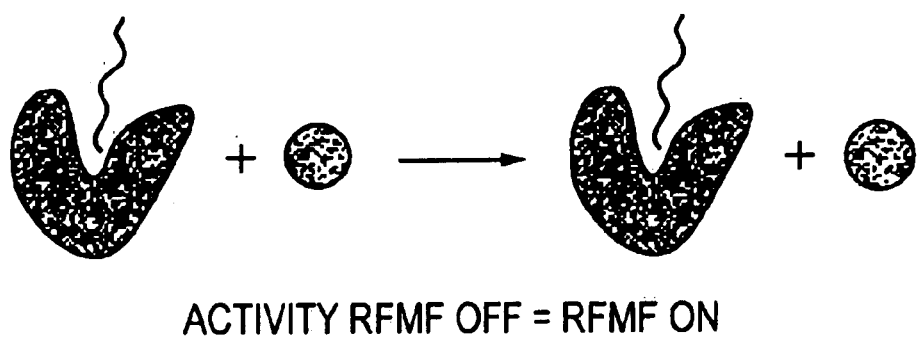

In this example, ribonuclease S was associated with a gold nanocrystal modulator (the system described in Example 1). The activity of the enzyme was controlled by induction heating of the modulator using an alternating magnetic field. The frequency of the alternating magnetic field was 1 GHz in the radiofrequency range. Accordingly, the alternating magnetic field is referred to as a radiofrequency magnetic field (RFMF). The modulator S-peptide and S-protein complex was incubated with the substrate, polyC, in solution at 37° C. The tube containing the sample was placed in a coil inside which the RFMF was generated and switched on. Activity was monitored by measuring the amount of digested polyC in the solution. PolyC was purified from the rest of the sample by precipitation with trichloroacetic acid (TCA). The activity was the amount of digested polyC, which is determined by the optical absorption of the sample at 280 nm. FIG. 9(b) shows the activity of a sample with the RFMF on and off as a function of reaction time. The activity with the RFMF on was less than with the RFMF off, indicating the RFMF affects the modulator S-peptide-S- protein complex to the point that the activity of the enzyme is decreased. Experiments with non-specifically bound modulators showed that this effect is specific. FIG. 5a shows the activity as a function of the modulator-S-peptide concentration with the RFMF on and off. The activity of the complex with the RFMF on was significantly less than with the RFMF off throughout the entire concentration range. When the modulator was not covalently linked to the S-peptide (FIG. 10(b)) the activity of the complex with the RFMF off and on was approximately the same. This demonstrated that the modulator must be linked to a specific portion of the protein for it to be effective in changing the activity of the complex, and not simply present in solution.

Estimates for energy input values were as follows: the energy for dissociation of the S-peptide-S-protein complex was 4.5 kcal/mol. However, as illustrated in this example, the energy from the RFMF was not sufficient to completely dissociate the peptide from the protein complex. Based on the experiments wherein modulators were associated with nucleic acids, the local temperature was raised by about 15° C. above the ambient temperature, which was estimated to be around 15 J/mol. It should be noted that when the sample was globally heated (i.e., in a water bath) to 45° C. or greater, the enzyme complex was irreversibly denatured and the enzyme activity was zero.

Example 3

Radio Frequency Regulation of Enzymatic Activity of Ribonuclease S

Figure 11:
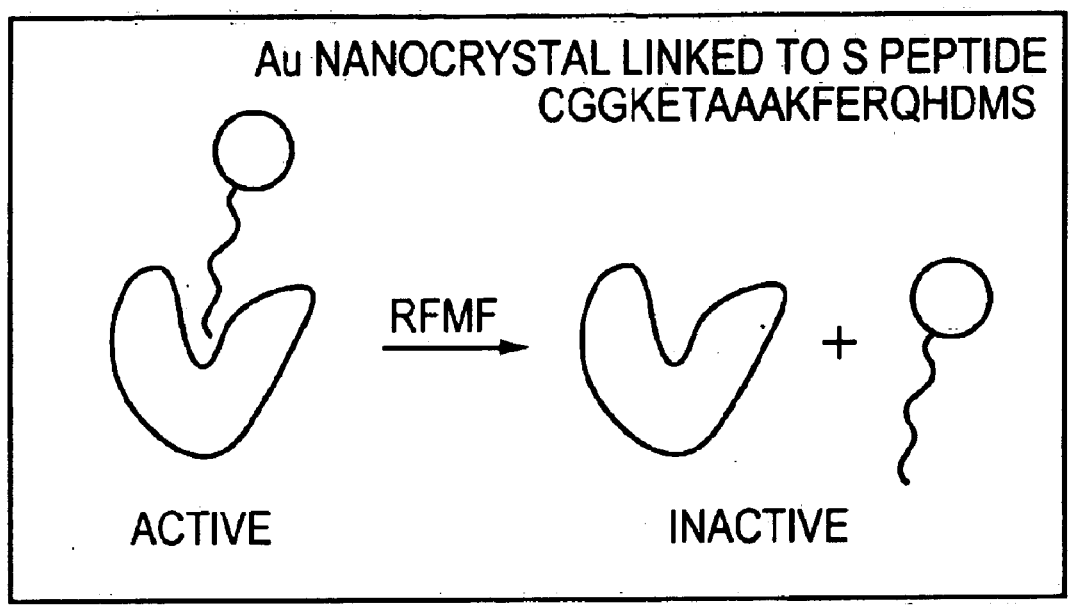
FIG. 11 illustrates the general scheme of Ribonuclease S modulation.

The ability to externally and remotely control biological systems at a higher precision with greater selectivity is a long-term goal for next generation of biological regulations. It is now possible to covalently link biological macromolecules with inorganic conducting particles, such as gold nanoparticle, or semi-conducting nanoparticles and have them respond to external electronic signals. The enzymatic activity if RNase S was precisely and selectively controlled by covalently attaching a single gold nanoparticle through a cysteine residue on the S-peptide of the ribonuclease S (RNase S) and then interacting it with the S-protein (FIG. 11). As shown in FIG. 11, the S-peptide was appended with three amino acids, two glycines and a terminal cysteine. It was subsequently attached to a nanocrystal (Au-S18) via the cysteine. The Au-S18 and S-peptide complex was active in that it was able to hydrolyze RNA. Under the radiofrequency magnetic field (RFMF), the Au-S18 binding to the S-peptide was weakened, rendering the activity of the entire protein off.

Figure 12A:
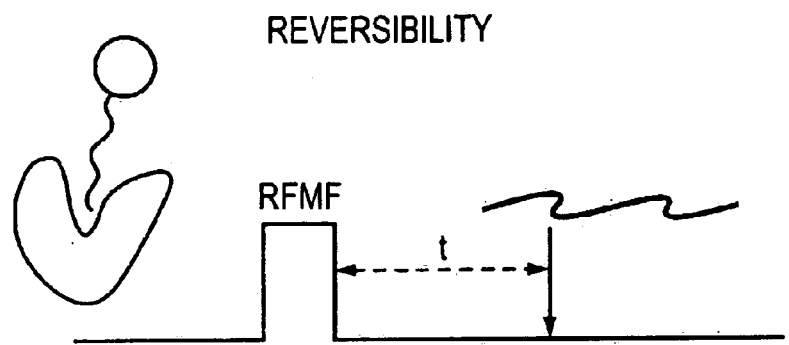
FIG. 12($a$) depicts a general schematic of an experiment demonstrating that the peptide is reversibly suppressed with the RFMF and not irreversibly damaged. The Au-S18/S-peptide system is exposed to RFMF, and after some recovery time the substrate is added. Activity is measured and compared to an identical sample that has not been exposed to RFMF.
Figure 12B:
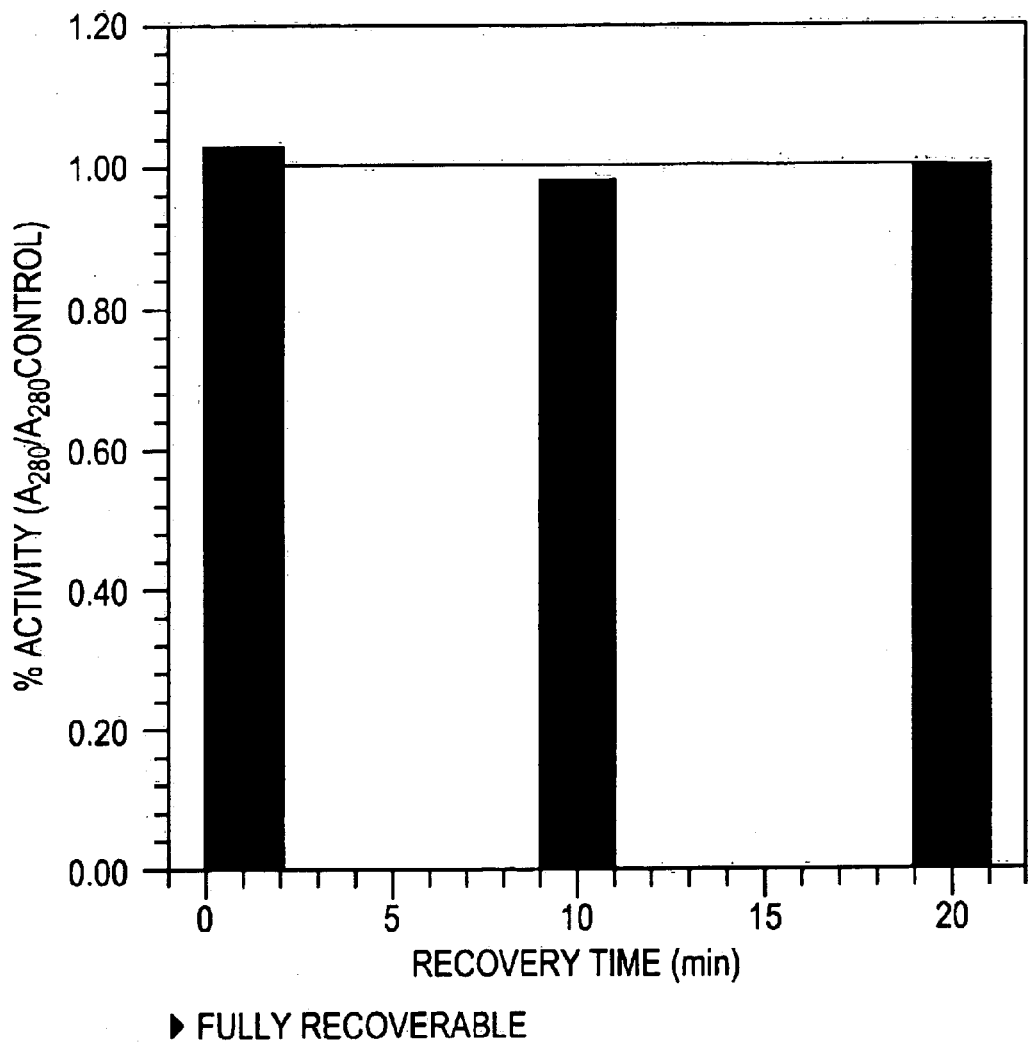

When the electronic radio frequency magnetic field (RFMF) of 1 Giga Hertz was applied to the gold nanoparticle linked S-peptide, it responded by transiently halting the enzyme activity. The enzymatic activity of the gold nanoparticle linked S-peptide with radio frequency control in the OFF state was indistinguishable from the S-peptide without the nanoparticles. This kind of RF controlled system is applicable to a broad range of biological regulations The reversibility of RF control of RNase S was also demonstrated by the experimental results (FIG. 12). The enzyme activity of the S-protein and S-peptide complex was turned ON and OFF through RF switch. This phenomenon most likely occurs through the partial deformation of the RNase S-substrate or protein complex. Since the complex of S-protein and Au-S18 peptide was deformed through RF input energy, it may temporarily denature the protein and dislodge the S-peptide from the protein complex, thus rendering its enzymatic activity in an OFF state. However, the S-peptide turned the enzyme ON again by reentering the S-protein pocket and reassembling the active complex. This process was repeated many times.

Further studies have also shown that the S-peptide with only the N-terminal 15 residues completely restored the enzymatic activity when combined with S-protein. According to the 3-D structure of RNase S, the S-peptide moiety is located in an open pocket of the S-protein, providing the N-terminus of the S-peptide some freedom of movement. Therefore RNase S provided a simple assay system to test the electronic control of enzymes. RNase S was used as a model system because both the S-protein and S-peptide are commercially available. The assay for RNase activity has already been well demonstrated, and it was easy to adapt the assay to measure the activity of reconstituted RNase S. A custom-designed small peptide was synthesized, i.e., an 18-residue peptide with an N-terminal cysteine and two glycines as spacer and the rest of the sequence that of the native S-peptide. A single gold nanoparticle was linked to the cysteine. The S18 peptide restored the RNase S enzyme activity upon combination with the S-protein. Furthermore, after covalently linking the gold nanoparticle to the S-peptide, the S-peptide was still fully active.

Figure 13A:
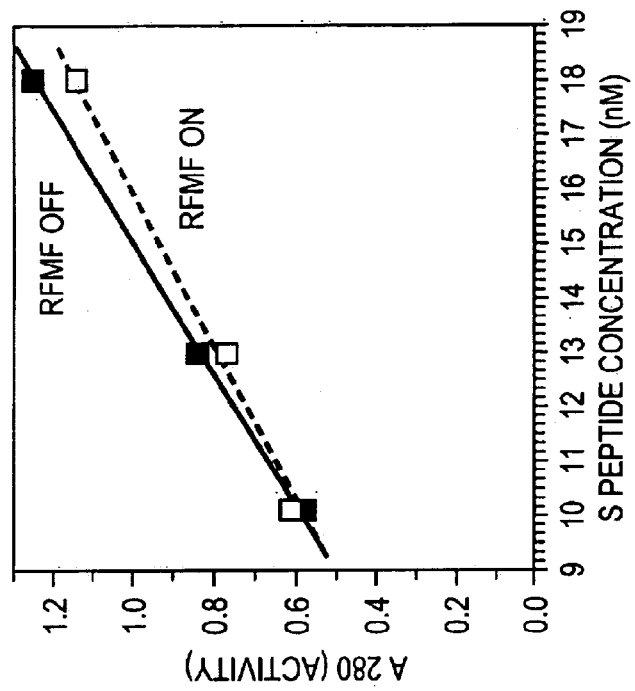
FIG. 13($a$) depicts a sample that has a nanocrystal linked to the S18. A280 is shown as a function of S18 and Au nanocrystal concentration with the RFMF on (dashed) and off (solid). The activity with the RFMF on is suppressed for the linked system (left).
Figure 13B:
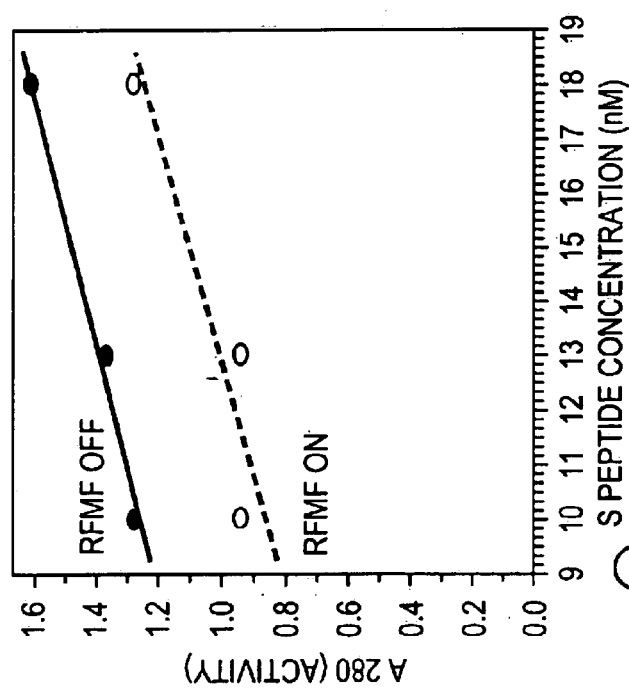

The gold nanoparticles that are not linked with the S18 peptide in the reaction mixture had no detectable effect in the enzyme reaction although, they also respond to the external RF (FIG. 13). This observation is important since it has previously been shown that gold nanoparticles could undergo inductive heating through the input of the RF energy.

Figure 14A:
FIG. 14($a$) depicts a general scheme for measuring protein activity modulated by RFMF. S18/S-peptide is exposed to its substrate, poly C, which it cleaves. At a fixed time, the reaction is halted by adding trichloroacetic acid (TCA), which acts by precipitating the Au-S18/S-peptide and any large uncleaved polyC. What remains in the supernatant is the hydrolyzed product, which is quantified by optical absorbance at 280 nm (A280).
Figure 14B:
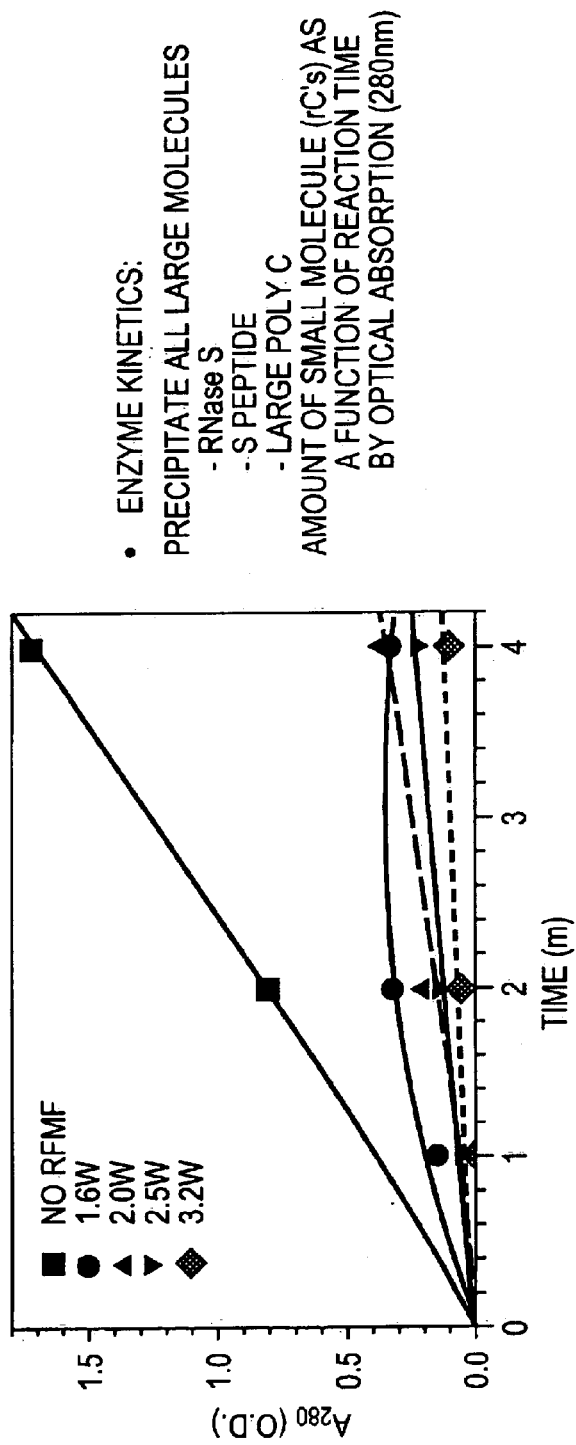

Since the RF energy input to the enzymatic reaction was precisely controlled, various levels of RF input to the reaction were tested (FIG. 14(b)). At low levels, e.g., –8 to –5 dBm, there was no significant effect on the RNase S activity using the Au-S18 peptide as the complex. On the other hand, when the RF levels increased to —4,–3,–2 to –1, there was a drastic effect on the enzyme activity. The RNase S no longer hydrolyzed poly C efficiently to produce the TCA soluble nucleotides. The narrow RF range between –5 and –3dBm with –4 dBm at the 50% activity demonstrated the fine control of RF. The effect was proportional to the RF power applied to the reaction indicating that the enzyme activity was completely regulated with the amount of electrical energy, a significant step in achieving electronic control of biomolecules.

Although RF has a drastic effect on the enzyme activity, the deformation of the effect can be recovered. This is similar to what has been shown for nucleic acids, in that when a DNA beacon is denatured, it can be readily renatured when RF is turned off. The recovery time was about 1 minute. Once it recovers, it remained fully active (data not shown).

It has been demonstrated that RF input can regulate biomolecules. Previously, it was reported that RF regulation of DNA beacon denaturation and renaturation occurs in a well-controlled manner. As demonstrated herein, proteins can be similarly regulated. This opens avenues for remotely and electronically controlling the regulation of intricate and complex biological systems in fine detail. Since the RF regulation does not involve any chemicals, nor any other non-recoverable substances, one can program a computer to control many biological processes in the future.

Covalently Linking a Peptide With a Gold Nanoparticle

The S18 peptide with the sequence, n-CGGKETAAAKFERQHMDS-c (SEQ ID NO.1), was synthesized and HPLC purified at Alpha Diagnostic (San Antonio, Tex.). The purity was nearly 100%, as judged by MASS spectroscopy.

The amino acid sequence from No. 4 to No. 18 (from N-terminal) was identical to that of No. 1 to No. 15 of the wild type S-peptide (S15), which exhibits full enzymatic activity when coupled with S-protein. The synthetic S18 peptide was modified to append three CGG residues to its N-terminus in order to covalently link the gold nanoparticle. Its enzymatic activity was indistinguishable from that of the S15 native peptide. The Cysteine was required to link the single gold nanoparticle and the two glycines serve as a spacer to avoid structural hindrance.

Monomaleimido nanogold labeling reagent was purchased from Nanoprobes Inc. (Yaphank, N.Y.). Thirty nano molar of nanogold reagent was dissolved in 0.1 ml isopropyl alcohol, and subsequently diluted to 1 ml with deionized and degassed water. 150 nM of S18 peptide was directly added to the gold nanoparticle solution, mixed well and incubated at 4° C. overnight and the reaction mixture was loaded on a Sephadex G25 column (1.1 cm×39 cm). Exclusion volume containing the gold linked peptide was collected.

Assay for RNase s Activity

The assay for measuring RNase activity was based on the measurement of increase in acid soluble nucleotides during the hydrolysis of poly-(C) (FIG. 14(a)). All concentrations were expressed as the final concentrations in the assay system. The S-protein (Novagen, Madison, Wis.) with various concentrations of S18 peptide was pre-incubated in 20 mM Na-phosphate buffer, pH 6.0; 100 mM NaCl at 37° C. for 10 minutes followed by initiating the reaction by the addition of the substrate, 0.39 mM poly [C] (sigma). At different time intervals, aliquots were quenched with 5% trichloroacetic acid (TCA). The reaction mixture was kept on ice for 5 minutes and subsequently spun at 13,000 rpm (Biofuge A) for 10 min. The absorbance of the acid soluble supernatant containing the nucleotides was measured at 280 nm for the extinction coefficient of cytosine which exhibits a maximal absorbance at 280 nm.

Application of Radio Frequency Magnetic Field (RFMF)

Alternating magnetic fields are generated by applying an electric current to a copper coil that coils around a quartz cuvette. Currents with frequencies in the radio frequency range are obtained by using a RF generator with a current amplifier. The RF is pulsed at 15 second intervals. The RF power levels are varied from −8 dBm to −0.1 dBm. The MF frequency used is 1 GHz.

Example 4

Control of Nucleic Acid Nano-assembler Using Modulators

Figure 15:
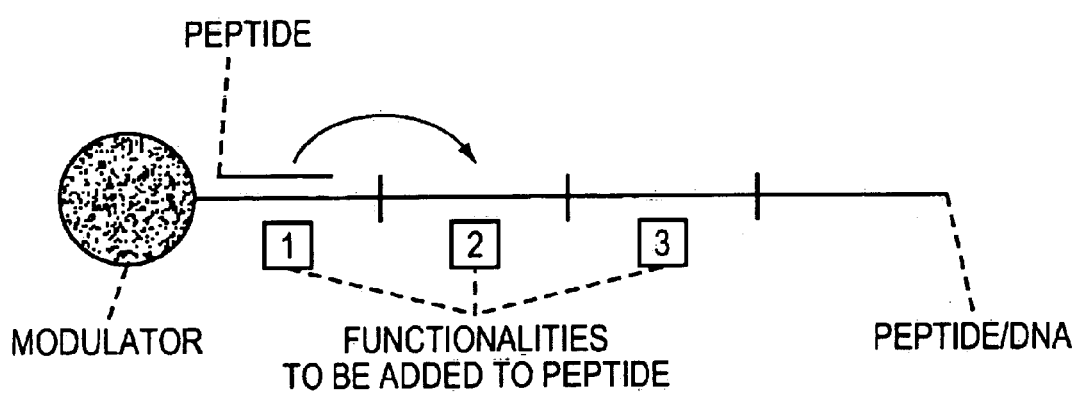
FIG. 15 depicts the control of a protein nano-assembler using modulators.

A modulator is attached to a series of modules (labeled 1, 2, 3), which are functionalities to be added to a protein in a specific order (FIG. 15). Each module carries out a different function to build up a final product. The protein is transferred from module to module and its transfer is dictated by the sequence in which a user addresses the various modulators by electromagnetic, magnetic, optical, or other physical means. The protein to be modified travels from module to module, each module carrying out a different function contributing to the final product. In another embodiment, the protein is attached to a bead that travels from module to module. This embodiment is especially useful in carrying out solid-phase synthesis on the bead (e.g., by means of an enzyme or other catalyst linked locally to each module). Examples of products that may be built using solid synthesis include an artificial polymerase, an artificial ribosome and an inorganic polymer.

Example 5

Radio-frequency Regulation of Protease Activity: Electronic Control of Thrombin Inhibitors for Conversion of Fibrinogen into Fibrin The protease activity of thrombin in vivo has been shown to be regulated by various endogenous inhibitors, including alpha2-macroglobulin, anti-thrombin III, heparin cofactor II, and nexin I. Other protein/peptide inhibitors of thrombin include the anti-coagulant hirudin, which is found in the saliva of the medicinal leech; rhodniin, and a variety of fragments of fibrin in the blood-sucking insect Rhodnius prolixus, that have a high affinity for thrombin. High-resolution crystallographic analyses have revealed that the alpha-thrombin molecule has a deep, narrow, canyon-like active site cleft, together with two positively charged patches, representing the fibrinogen-recognition exosite and the heparin binding site. These sites are critical for thrombin function and also for its interaction with both substrates and inhibitors.

When these inhibitors bind tightly to the deep cleft of thrombin to form a noncovalent complex, they impede thrombin enzymatic activity, resulting in the loss of function to cleave fibrinogen to produce fibrin. Consequently, no fibrin matrix sealant is available for coagulation. This very high affinity interaction provides a unique opportunity to control the thrombin activity with RF.

Alpha-thrombin inhibitors, fibrinogen and various fibrin fragment inhibitory peptides are commercially available or can be made synthetically. Anti-fibrin antibody and fibrin proteins are also available. The protocols for conducting the following experiments are widely used and well standardized. All other reagents, the RF device and RF generator as well as measurement instruments are readily available.

An anticoagulation protein (Hirudin, from leech saliva) has an extremely high affinity for thrombin and inhibits the enzymatic cleavage of fibrinogen by thrombin. A fragment of Hirudin called hirugen53-64 peptide also has a very high affinity for thrombin. This hirugen53-64 peptide is linked with gold nanoparticles and subjected to RF control. Furthermore, several fibrin gamma chain fragment peptides, 408-427 and 414-427, have been demonstrated to strongly inhibit thrombin activity, especially the ones with sulfated tyrosines and negative charges on the peptides. These peptides play a key role in the inhibition process, likely due to the complementary interaction with the positively charged cleft of thrombin. Peptides with phosphorylated tyrosines are also used in inhibition assays because phosphate further enhances the negative charges on the peptide. The first six amino acid residues, Cys-Gly-Ala-Gly-Ala-Gly, (CGAGAG) (SEQ ID NO.2) are artificially added as a linker to extend the peptide for gold nanoparticle linkage.

Several peptides that have been investigated and demonstrated to play a role in the inhibition of thrombin activity are commercially available. These are listed in table 1.

TABLE 1

Thrombin inhibitory peptide and derivatives that will be used in the study

| Name | Sequence (N-->C) | |
|---|---|---|
| | ☐     + -+  - -*-  * ---  | |
| Fibrin408-27 | CGAGAG-VRPEHPAETEYDSLYPEDDL | (SEQ ID NO.3) |
| | ☐    - -*-  * --- | |
| Fibrin414-27 | CGAGAG-AETEYDSLYPEDDL | (SEQ ID NO.4) |
| | ☐    - --  --* | |
| Hirudin53-64 | CGAGAG-NGDFEEIPEEYL | (SEQ ID NO.5) |
| PPACK | D-Phe-L-Pro-L-Arg-chloromenthy ketone | |

The above-mentioned peptides are readily purchased or synthesized, purified by HPLC and characterized by mass spectrometry. ☐ denotes the cysteine where the gold nanoparticle is covalently linked. − and + denote the negatively and positively charged residues and * denotes sulfated tyrosine residues. Peptides with phosphorylated tyrosines are also used in the inhibition assay. Since the C-terminus of the peptides is found to be critical for thrombin high affinity binding, it remains unaltered. As the sequence of fibrin414-427 is functionally equivalent to fibrin 408-427, the N-terminus VRPEHP (SEQ ID NO.6) is removed. Hirudin 53-64 has a very high affinity for thrombin, resulting in a inhibitory effect. PPACK is not used for RF regulation; rather, it is used as a positive control since its inhibitory effect on thrombin is well documented.

Covalently Linking Gold Particles to the Inhibitory Peptides

Thirty nano moles of a gold nanoparticle reagent are dissolved in 0.1 ml isopropyl alcohol and subsequently diluted to 1 ml with deionized and degassed water. 150 n moles of thrombin or fibrin inhibitory peptides are directly added to the gold nanoparticle solution, mixed well and incubated at 4° C. overnight. The reaction mixture is subsequently loaded on a Sephadex G25 column (1.1 cm×39 cm), and exclusion volume containing the gold linked peptides is collected.

Application of RFMF

Alternating magnetic fields are generated by applying an electric current to a copper coil that coils around a cuvette. Currents with frequencies in the radio frequency range are obtained by using a RF generator with a current amplifier. The RF is pulsed at 15 second intervals or at a different time pulse. The RF power levels are varied from −8 dBm to −0.1 dBm. An RFMF frequency of 1 GHz is used.

RF controlled protease activity systems is used to study a broad spectrum of biological regulations including various types of biomolecular interactions, study of protein folding and protein-protein interactions, thus resulting in the regulation of signal transduction, cell cycle, and cellular reprogramming.

Figure 16:
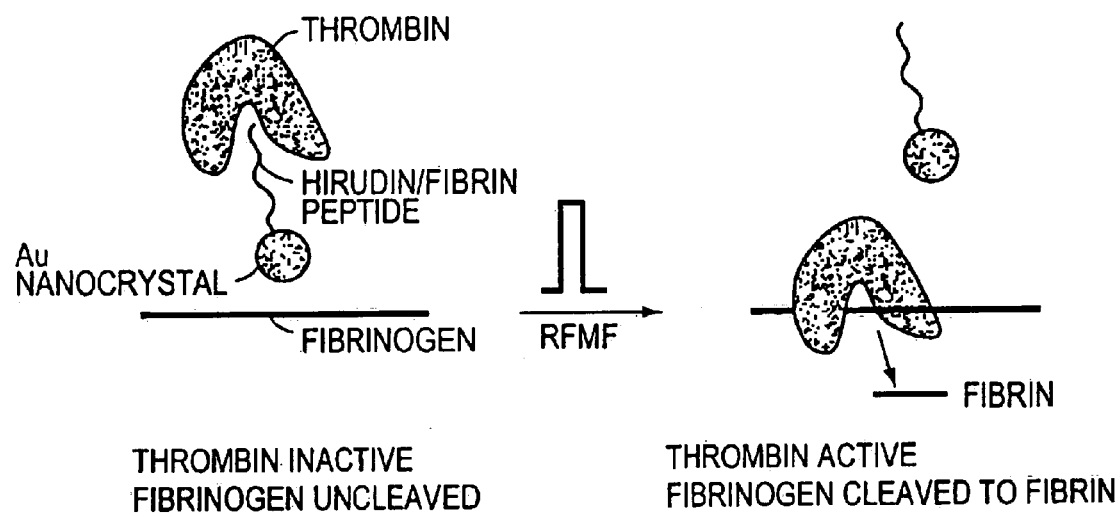
FIG. 16 schematically illustrates the RF thrombin activity assay.

Assay of RF Controlled Thrombin Enzymatic Activity and Fibrin Inhibitory Peptide A series of vials containing fibrinogen in the presence or absence of thrombin and thrombin inhibitory peptides are used in systematic assays (FIG. 16). These include concentration curves for various enzyme-substrate combinations, the time course, the temperature curve, pH curve as well as the RF power, duration and pulse curves. Previous studies of Ribonuclease S and DNA beacon provide a strong basis to carry out these experiments.

The concentration of fibrinogen remains constant in the assay at the beginning. In the first series of experiments, an increased amount of thrombin is used to produce a curve of optimal enzymatic activity. After both optimal concentrations of fibrinogen and thrombin are determined, a series of gold nanoparticle linked fibrin inhibitory peptides are added and the time course experiment is conducted. These experiments are carried out in such a way that the complex between thrombin and an inhibitory peptide is first incubated for an hour, subsequently followed by the addition of fibrinogen to the complex. RF is applied at various times after the addition of the substrate, fibrinogen. Fibrin is produced only if thrombin remains active.

The product of fibrin is assayed with a variety of methods including antibody immune-precipitation, gel electrophoresis and western blot, as well as fibrin gelation assay. The combination of these complementary assays provide information on RF regulation of the thrombin protease activity (FIG. 17).

Figure 18:
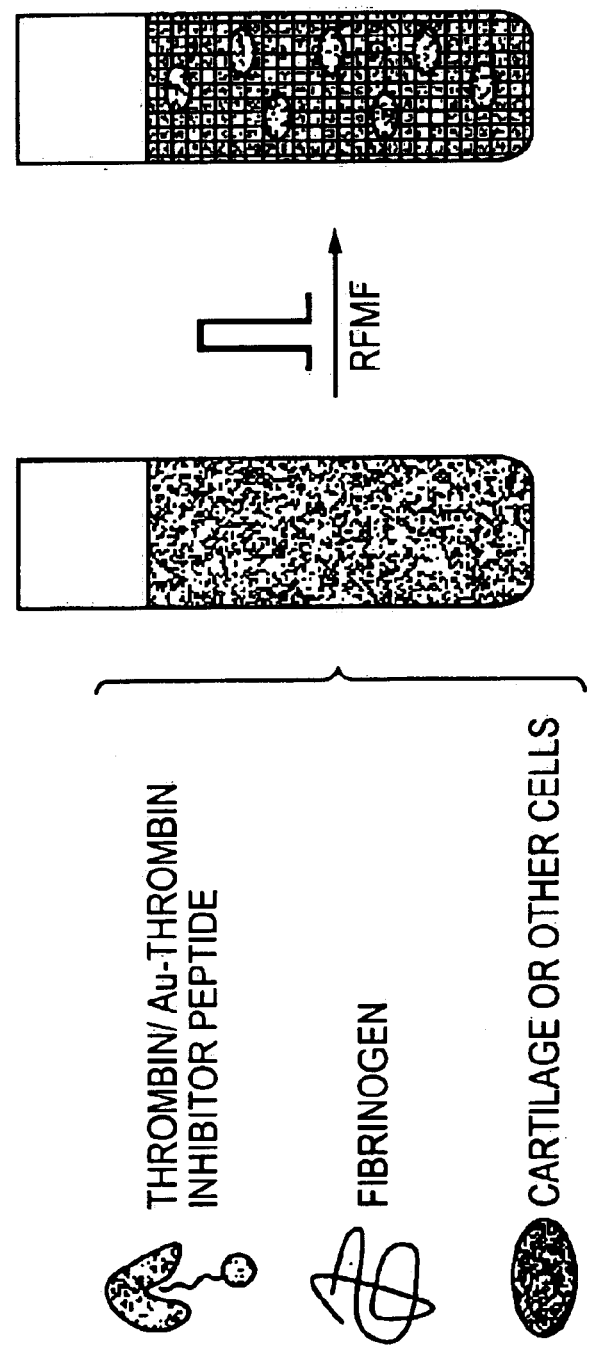
FIG. 18 depicts the use of a cell-based sealant.

A tube of liquid or semi-liquid fibrinogen solution is carried in the presence of the thrombin-inhibitory peptide complex that is under RF regulation. As and when needed, the protein solution is poured on to the wound area and the hand-held RF device is applied to activate the thrombin enzymatic activity, thereby to produce fibrin matrix sealant. Furthermore, cells and cartilage pieces are also included in the wound healing solution to formulate a cell-based matrix that accelerates the acute wound healing process (FIG. 18). This kind of simple RF activated acute wound healing systems provides critical time needed for saving lives.

Example 6

Construction of Peptide/Protein Electronic Nanowires and Nanoswitches

Figure 19:
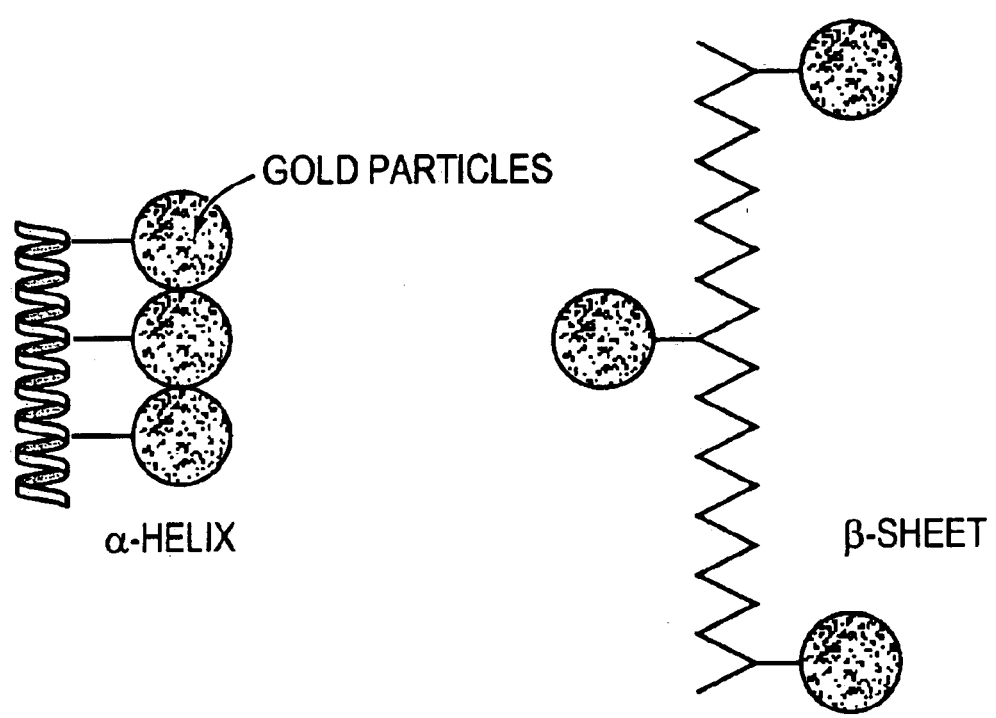
FIG. 19 is a schematic drawing of a small nanoparticle on helical and extended beta-strand.

A great deal of work has been carried out to rationally design new functionality of known proteins and even new proteins [Blundell, 1994; Harbury, et. al., 1998]. Although β-sheets have recently been considered as building materials to produce nano-tapes, molecular-straw and molecular Lego [Aggeli, et al., 1997], α-helices still remain under-explored as nano-construction building block materials for applications outside of biology. A type of dipolar peptide that undergoes a drastic structural transition under influence of temperature and pH was recently described [Zhang & Rich, 1997, Altman, et. al, 2000]. These monomeric stable helices have a cluster of negatively charged residues located near the N-terminus and positively charged residues located near the C-terminus. However, when the helical dipole is reversed, it lost its helix forming capability [Zhang & Rich, 1997, Altman, et. al., 2000]. As shown in FIG. 19, when one member of these peptides, the 16-residue peptide DAR16-IV, is in the β-strand form, it has a total length of approximately 5 nm but when it is in a helical form, it has a compressed length of approximately 2.4 nm. This kind of conformational change is readily developed as a molecular nanoswitch.

Construction of Stable Monomeric Helical Peptide Nanowires

A variety of monomeric helical peptide nanowires are synthesized and well characterized. These peptides are linked with gold nanoparticles to form nanowires and nanoswitches. These nanowires and nanoswtiches are subsequently tested for various properties.

Construction of di-tri- and tetra-coiled Coil Peptide/protein as Scaffold

A number of coiled coil peptides and proteins have been well investigated. The dimeric and trimeric peptides/proteins with the typical coiled coil motifs are synthesized and their structure and stability are characterized. These peptides/proteins linked with gold nanoparticles are used as a scaffold to organize the gold nanoparticles into ordered structures. Through the coiled coil interactions, the nanoparticles will undergo self-assembly in a controlled manner.

Well-known helical proteins, such as di- coiled-coil (found in keratin, myosin), tri- and tetra-helical coiled-bundle are used to develop different type of nanowires. Such nanowires not only have increased stability but also enhanced conducting capability. The length of the nanowire is calculated and adjusted through peptide condensation, or the production of long helical proteins using genetic engineering technology. Furthermore, many other repeating motifs found in some fibrous proteins, such as triple helical structure of collagen, extended beta-sheet of silk fibroin and a new beta-helix found in spider silk are molecularly engineered to produce a spectrum of nanowires for a number of nanotechnology applications.

Stable alpha-helical peptide and proteins, by definition, are nanostructures because they possess well-defined structural dimensions [Pauling, 1960; Branden & Tooze, 1999]. There are a number of ways to construct peptide and protein helical structures that are further modified and functionalized to incorporate different residues into nanowires and nanoswitches. There is a wealth of information for atomic resolution of helical structures in peptides and proteins [Branden & Tooze, 1999]. Extensive modeling and theoretical calculations on the formation of helices have been carried out [Barlow & Thornton, 1988; Aurora & Rose, 1998]. These helical structures are designed as monomeric, dimeric, trimeric or tetrameric helices [Hecht, et. al. 1990; Woolfson & Alber, 1995; Ogihara, et. al., 1997; Kajava, et. al., 1995, Marqusee & Baldwin, 1987; Zhang & Rich, 1997, Zhang, unpublished results].

Molecular Self-assembly of the Nanoparticles to form a Nanowire and Clusters of Nanowires.

The coiled-coil peptide/proteins at various concentrations, i.e., average number of peptides, 2, 3, 4, 5 or more peptides per nanoparticle, are systematically tested. Different sizes of nanoparticles, i.e., 1 nm, 2 nm, 5 nm, 10 nm and 20 nm with limited number of peptides are linked and systematically tested. The two different systems produce quite different nanowire and nanoswitch properties.

Measurement of the Peptide/protein Nanowires and Nanoswitches

The conductivity and other electrical properties of these peptide/protein nanowires and nanoswitches is determined. First, the nanometer scale devices are fabricated. This task is readily achievable through nano-printing technology. The electrical and electronic properties are subsequently tested for a variety of parameters.

The class of dipolar oligopeptides described below is able to undergo drastic structural transitions under influence of temperature and pH (perhaps magnetic field or electric energy). These 16 residue peptides form both typical beta-sheets and alpha-helices. When these peptides are in the beta-sheet form, the peptide amide backbone is extended 3.4 Å per residue with a total length of approximately 5 nm. On the other hand, in the helical form, the backbone is coiled, like a spring, with 1.5 Å per residue and a length of approximately 2.3 nm. This modulated conformational change is developed as a peptide/protein molecular electronic nanowire.

New type of alpha-helical peptides and proteins are synthesized by incorporating thio-containing cysteine residues on every $14^{th}$ and $28^{th}$ position, approximately every 2.1 nm and 4.2 nm, respectively, such that the cysteine residues are located on the same side of the helix. Because each residue has 100° per turn, every $14^{th}$ residue is 1400°/360°, which is close to 4 fall turns of helix. These cysteine residues covalently bind gold nanoparticles (1.4 nm), which are located on the helical peptide chain every 2 nm (0.15 nm×14=2.1 nm). When the helical structure is induced to change to beta-strand/sheet form, the distance between the cysteine residues changes to 2.1 nm ($14^{th}$) and 4.2 nm ($28^{th}$). Such a well-regulated nanostructure is designed, tailored and fabricated at the molecular level with extremely high precision. Therefore, a variety of helical structures are readily designed and constructed for a broad range of nanowires and peptide and protein-based nanoswitches. The length of the peptide building units is calculated in Table 1. For example, by incorporating cysteines at positions 1, 14, and 28, the cysteines are spaced approximately every 2.1 nm. Thus the peptide will have cysteines approximately 2.1 nm apart when it is in α-helical form and 4.8 nm apart when it is in β-strand form. Gold nanoparticles are covalently linked to the thio-group of cysteines. Therefore, when the peptides are in the helical form, the gold nanoparticles overlap and a tunneling event takes place, whereas, when the peptides are in the extended strand form, it loses conductivity due to the extended distance of the gold nanoparticles. The peptide and protein nanowire is further developed as a molecular switch or an actuator for nanostructural devices. One way this is accomplished is by attaching the peptide nanowires to printed electrodes of a silicon circuitry through covalent thio-gold linkage. An electronic source modulates the structural changes of the peptide. There is also a drain that measures the conductivity from the peptide/protein nanowire. This allows the measurement of various conducting and semiconducting events through the structural transitions of the peptides. This new class of molecular switches is extremely versatile and is readily designed, tailored, and modified through well-known detailed molecular structural information.

TABLE 1

Distances and angles of dipolar peptides in α-helical and β-strand

| Peptide (AA) | # bonds | α-helix form (0.15 nm/100°/AA) | β-form (0.34 nm/180°/AA) |
|---|---|---|---|
| 12 | 11 | 1.65 nm (1100/360 = 3 turns) | 3.74 nm |
| 15 | 14 | 2.1 nm (1400/360 = 3.9 turns) | 4.76 nm |
| 19 | 18 | 2.7 nm (1800/360 = 5 turns) | 6.12 nm |
| 30 | 29 | 4.2 nm (2900/360 = 8 turns) | 9.86 nm |
| 37 | 36 | 5.4 nm (3600/360 = 10 turns) | 12.24 nm |

The above calculations are based on information from crystal structures of α-helices and β-sheet in proteins

[Pauling, 1960, Cantor & Schimmel, 1980; Creighton, 1993; Branden & Tooze, 1999]. In α-helical form, each residue is at 1.5 Å and 100° per translation; whereas, in a β strand form, each residue is at 3.4 Å and 180° per translation. The number of helical turns is calculated using the total number of degrees divided by 360°, which constitutes one full turn of helix.

Design Stable Monomeric Helical Peptides

Several monomeric helical dipolar peptides (Table 2) are readily synthesized. These peptides are derived from a group of peptides that are well studied. These peptides have specific dipoles with negative charges at the N-terminus and positive charges at the C-terminus. In these experiments, specific residues amenable to linkage (i.e. thio) are incorporated at defined positions. Using these linkages, nanogold particles are attached to the peptides to produce an electronic molecular switch. Additional metallic nanoparticles are attached at $1^{st}$, $18^{th}$ and $37^{th}$ residues, further providing electronic contacts to the outermost metallic nanoparticles that constitute an electronic molecular switch in which the two conformations have markedly different tunneling currents. A RF pulse tuned to the resonance of such a nanostructure induces a local perturbation of the peptide structure thus transitioning the peptide from an α- to β-conformation. There are nanogold particles of several distinct sizes, the 2 nm nanoparticle being quite suitable for linking to the peptides/proteins listed in table 2. 1.4 nm gold nanoparticles are used for a peptide unit of 12 residues (Table 1).

to form a hydrophobic core. Several dimeric and trimeric helical bundles (Table 3) have been designed and additional ones can also be designed. The dCoil-GCN is derived from a native transcription factor in yeast [O'Shea, et. al, 1991] and dCoil-L and dCoil-LA are well known in the art. Three cysteines are added at positions 1, 14 and 30 that correspond to the nanogold spacing which is about 2 nm and at positions 4 and 8, which are helical turns for dCoil-L29. The tCoil-L29 peptides that form trimers are derived from a segment found in the protein tropomyosin [Sodek, et al., 1972; Lau, et al., 1984]. The tCoil-V29 is the derivative of tCoil-L29 where the 4 leucines have been changed to valines [Ogihara, 1997]. Crystal structures for most of these peptides have been determined.

The basic building units of the coiled coil motif occur in three different forms (Table 3). These coiled coils and coiled bundles are very stable even at high temperatures in solution (Harbury, et. al., 1993). The selected sequences of dimeric, trimeric and tetrameric peptides have typical coiled coil motifs where every $7^{th}$ residue is a leucine [Branden & Tooze, 1999]. Positions a and d are usually hydrophobic residues, L, I, V, F, Y, M, A; positions e and g are often complementary charged residues, E, D, K and R; positions b, c, and f are not stringently conserved. The dCoil-GCN

TABLE 2

Construction of stable monomeric helical peptide units

| Name | Sequence | Unit length (nm) α-form | Unit length (nm) β-form |
|---|---|---|---|
| CEAK15 | CEAEAEAKAKAKAKC (SEQ ID NO.7) | 2.1 | 4.42 |
| CDAR15 | CDADADADARARARC (SEQ ID NO.8) | 2.1 | 4.42 |
| CDAR15 | CDDDDAAAAAARRRC (SEQ ID NO.9) | 2.1 | 4.42 |
| CEAK15 | CEEEEAAAAAAKKKC (SEQ ID NO.10) | 2.1 | 4.42 |
| CDAR15 | CDDDDAAAAAARRRC (SEQ ID NO.11) | 2.1 | 4.42 |

These peptides provide examples of nanowires/nanoswitches and are synthesized. The distances between the cysteines where the gold nanoparticle is linked is listed in two different forms. When the peptides are in α-form, the distance is short, allowing the nanogold particle to overlap leading to the formation of a tunnel conducting state, whereas, when the peptide is in the β-form, the nanogold particle can no longer overlap, thereby resulting in weakening or loss of the conductivity.

Design Dimeric and Trimeric Helical Coiled-coils for Nanowires and Nanoswitches

The dimeric and trimeric peptides have the typical coiled coil motifs where every 7th residue is a leucine at positions a and d, also called 4, 3 hydrophobic sequence repeats [Landschulz, et. al., 1988; O'Shea, et. al, 1991; Ogihara, et. al., 1997; Branden & Tooze, 1999]. These leucines interact was derived from a native protein which is a transcription factor in yeast [O'Shea, et al, 1991]. The tCoil-GCN29 tricoil bundle was derived from the GCN4 protein where the residue at position a is replaced by Leu and the residue at position d is replaced by Ile (Harbury, et. al., 1993, 1995). Crystal structures for most of these peptides have been determined.

After these peptides are made, nanogold particles are attached to the peptides using conventional protocols available from the suppliers and on the web. These modified peptides are subjected to extensive experimental tests for their ability to undergo conformational changes under various external influences. Such changes are monitored by various systems including circular dichroism (CD), FTIR, and NMR.

TABLE 3

Building unit of di-, tri- and tetra- coiled-coil and coiled bundles

| Name | Sequence | Unit length (nm) |
|---|---|---|
| Dimeric coiled coils | | |
| Positions | abcdefg abcdefg abcdefg abcdefg | |
| dCoil-adIL29 | C IKQLEDK IEELLCK IYHLENE IARLKCL (SEQ ID NO.12) | 4.2 |
| dCoil-adLL29 | C LADLEKR LDELACK LEDAAKR LQSLACK (SEQ ID NO.13) | 4.2 |
| dCoil-LA29 | C LAALEAR LAALECR LAALEAR LAALECR (SEQ ID NO.14) | 4.2 |
| Trimeric bundle | | |
| tCoil-LL29 | C LEALEKK LAALECK LQALEKK LEALECH (SEQ ID NO.15) | 4.2 |
| tCoil-adII29 | C IKQIEDK IEEILCR IYHIENE IARIKCK (SEQ ID NO.16) | 4.2 |
| tCoil-IQN29 | C MKQIEDK IEEIECK QKKIENE IARIKCK (SEQ ID NO.17) | 4.2 |
| tCoil-IQI29 | C MKQIEDK IEEILCK QYHIENE IARTKCK (SEQ ID NO.18) | 4.2 |
| Tetrameric bundle | | |
| qCoil-adLI29 | C LKQIEDK LEEILCK LYHIENE LARIKLC (SEQ ID NO.19) | 4.2 |

Design Collagen Triple-helix for Nanowires and Nanoswitches

The polyproline type II collagen is a trimeric helix with a 0.96 nm unit per turn along the axis with 3.3 residues (Rich & Crick, 1961; Bella, et. al., 1994). Each residue is extended to 0.291 nm per rise. This is very different from the alpha-helix which has 0.54 nm per turn with 3.6 residues, each residue having a rise of 0.15 nm. The collagen triple helix is used to produce nanowires and nanoswtiches (Table 4).

TABLE 4

Basic building units of collagen helical wires

| Name | Sequence (N->C) | | Unit Length (nm) |
|---|---|---|---|
| PXY24 | CPPGPPGPCGPPGPPGCGPPGPPC | (SEQ ID NO.20) | 7 |
| PXY34 | CPPGPPGPCGPPGPPGCGPPGPPCGPPGPPGPPC | (SEQ ID NO.21) | 10 |

Directly Link Nanozold Onto Helical Heptide and Proteins

It has been well established that covalently linking nanogold particles to proteins, such as antibodies and others, is a standard practice in electron microscopy and other imaging techniques. Both colloidal and monoaleimido gold nanoparticles are readily available commercially (Ted Pella, Inc., Reading, Calif.; Nanoprobes, Stony Brook, N.Y.). The protocol for attachment has been well established. Effective attachment of nanogold particles to peptides has been performed and used in various experiments. The linking reaction is conducted in the absence of oxygen.

Molecular Self-assembly of Peptide/protein Nanowires

Figure 20:
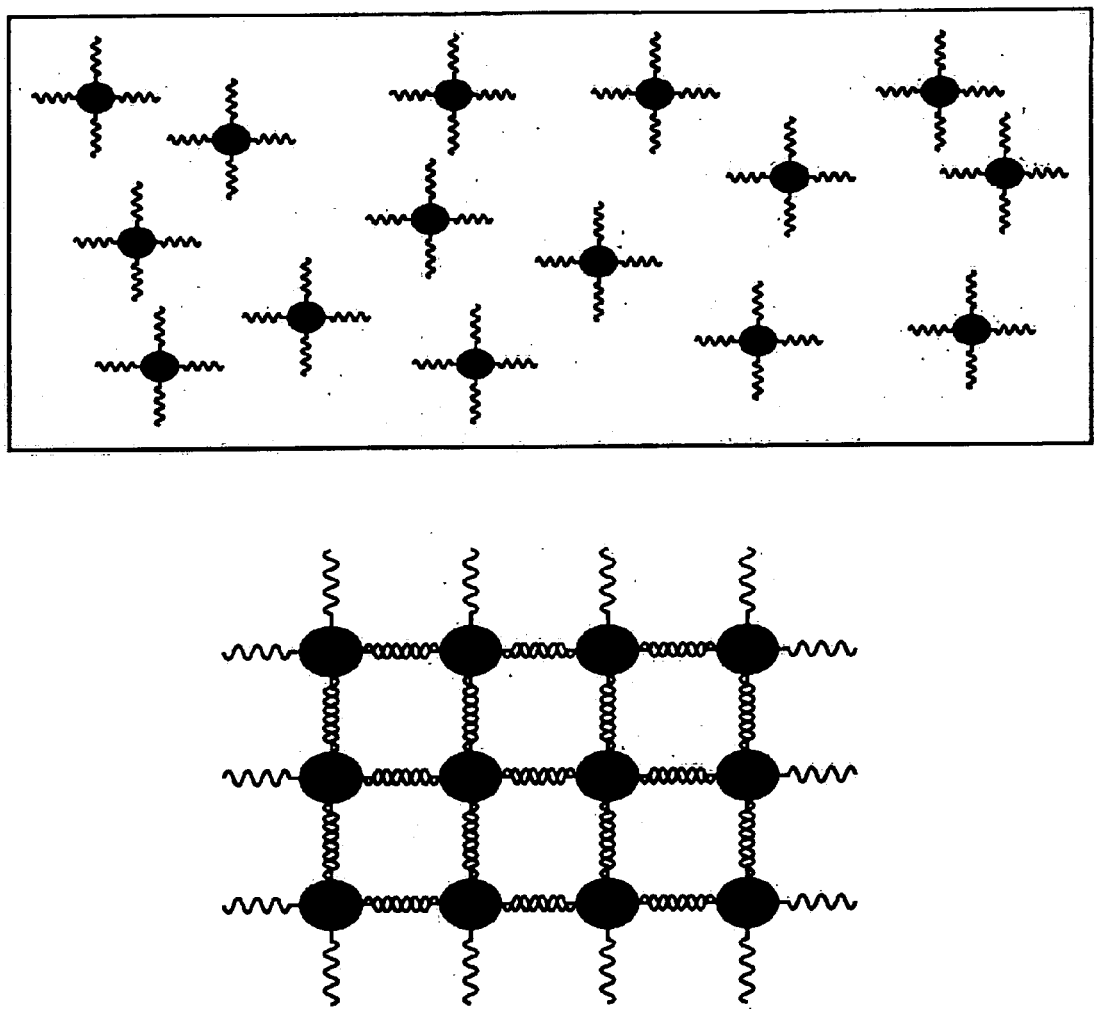
FIG. 20 depicts an individual gold nanoparticle linked to a peptide/protein and a cluster formation of gold nanoparticles linked to a peptide/protein.

A peptide/protein serves as the scaffold for gold nanoparticle cluster formation. The peptide/protein linked gold nanoparticles in solution undergo molecular self-assembly to form gold nanoparticle clusters (FIG. 20). This task is readily achieved by incubating the individually labeled gold particles at various conditions, i.e., different concentrations, temperatures and pHs. The assembled clusters are monitored through the range of spectrum and the occurrence of precipitation is visualized. The distance, flexibility and the extent between the gold nanoparticles is adjusted in the design of the peptide and in the choice of the gold nanoparticles. More than one peptide/protein is linked to one nanoparticle depending on the particle size. The larger the nanoparticles, the larger the number of peptides that are linked together. The extent of the linkage is also dependent on the peptide/protein concentration. For example, the 1.4 nm gold nanoparticles allow only a few peptide linkages on the particle, whereas, the 2 nm particles permit more peptide linkages. Likewise, 5 nm and 10 nm nanoparticles allow more peptide/protein linkages. By varying the size of the gold particle and the concentration of the peptide/protein, an array of different and interesting nanowires are produced.

Although the present invention has been described with reference to specific details, it is not intended that such details should be regarded as limitations upon the scope of the invention, except as and to the extent that they are included in the accompanying claims.

What is claimed is:

1. A method for remotely altering the structure of a protein, the method comprising the steps of:
   covalently or non-covalently linking a nanoparticle with a protein, wherein said nanoparticle is selected from the group consisting of metal nanoparticles and semiconducting nanoparticles; and
   exposing the nanoparticle to an external field, wherein the external field is selected from the group consisting of a magnetic field, an electric field, and an electromagnetic field, the external field causing the nanoparticle to alter the structure of the protein.

2. The method of claim 1, wherein said nanoparticle is non-covalently linked to said protein.

3. The method of claim 1, wherein said nanoparticle is covalently linked to said protein.

4. The method of claim 1, wherein said nanoparticle is selected from the group consisting of organic and inorganic modulators that are responsive to an external field.

5. A method for remotely altering the structure of a protein, the method comprising the steps of:
   covalently or non-covalently linking a nanoparticle with a protein, wherein said nanoparticle is selected from the group consisting of non-colloidal gold, colloidal gold, silicon, ruthenium, cadmium selenide, gold maleamide, and N-hydroxysuccinimidyl gold; and
   exposing the nanoparticle to an external field, wherein the external field is selected from the group consisting of a magnetic field, an electric field, and an electromagnetic field, the external field causing the nanoparticle to alter the structure of the protein.

6. The method of claim 1, wherein said nanoparticle transfers energy to protein upon exposure to said external field.

7. The method of claim 1, wherein said nanoparticle heats said protein upon exposure to said external field.

8. A method for remotely altering the structure of a protein, the method comprising the steps of:
   covalently or non-covalently linking a nanoparticle with a protein; and
   exposing the nanoparticle to an external field, wherein the external field is selected from the group consisting of a magnetic field, an electric field and an electromagnetic field, and wherein said nanoparticle cools said protein upon exposure to said external field, the external field causing the nanoparticle to alter the structure of the protein.

9. A method for regulating transcription, the method comprising the steps of providing a modified transcription repressor covalently or non-covalently linked to a nanoparticle that is responsive to an external field, wherein the modified transcription repressor binds to a gene to inhibit transcription; and exposing the modified transcription repressor to an external field, wherein the external field is selected from the group consisting of a magnetic field, an electric field, and an electromagnetic field, the external field causing the nanoparticle to alter the structure of the modified transcription repressor and alter the binding of the modified transcription repressor to the gene.

10. The method of claim 1, wherein the exposing step affects enzymatic activity.

11. The method of claim 1, wherein the protein is capable of polymerization and the exposing step affects the polymerization of said protein.

12. The method of claim 1, wherein the exposing step affects the structural stability of said protein.

13. A method for remotely altering the structure of a protein, the method comprising the steps of:
   covalently or non-covalently linking a nanoparticle with a protein; and
   exposing the nanoparticle to an external field, wherein said protein is an ion channel, and
   wherein ion flow through said ion channel is controlled by the step of exposing said nanoparticle to an external field and, wherein the external field is selected from the group consisting of a magnetic field, an electric field, and an electromagnetic field, the external field causing the nanoparticle to alter the structure of the protein.

14. The method of claim 13, wherein said ion channel is located in a biological membrane.

* * * * *

SEQUENCE LISTING

<160> NUMBER OF SEQ ID NOS: 21

<210> SEQ ID NO 1
<211> LENGTH: 18
<212> TYPE: PRT
<213> ORGANISM: Artificial Sequence
<220> FEATURE:
<223> OTHER INFORMATION: S18 peptide

<400> SEQUENCE: 1

Cys Gly Gly Lys Glu Thr Ala Ala Ala Lys Phe Glu Arg Gln His Met
1               5                   10                  15

Asp Ser

<210> SEQ ID NO 2
<211> LENGTH: 6
<212> TYPE: PRT
<213> ORGANISM: Artificial Sequence
<220> FEATURE:
<223> OTHER INFORMATION: Linker peptide

<400> SEQUENCE: 2

Cys Gly Ala Gly Ala Gly
1               5

<210> SEQ ID NO 3
<211> LENGTH: 26
<212> TYPE: PRT
<213> ORGANISM: Artificial Sequence
<220> FEATURE:
<223> OTHER INFORMATION: thrombin inhibitory peptide: fibrin 408-27

<400> SEQUENCE: 3

Cys Gly Ala Gly Ala Gly Val Arg Pro Glu His Pro Ala Glu Thr Glu
1               5                   10                  15

Tyr Asp Ser Leu Tyr Pro Glu Asp Asp Leu
            20                  25

<210> SEQ ID NO 4
<211> LENGTH: 20
<212> TYPE: PRT
<213> ORGANISM: Artificial Sequence
<220> FEATURE:
<223> OTHER INFORMATION: thrombin inhibitory peptide: fibrin 414-27

<400> SEQUENCE: 4

Cys Gly Ala Gly Ala Gly Ala Glu Thr Glu Tyr Asp Ser Leu Tyr Pro
1               5                   10                  15

Glu Asp Asp Leu
            20

<210> SEQ ID NO 5
<211> LENGTH: 18
<212> TYPE: PRT
<213> ORGANISM: Artificial Sequence
<220> FEATURE:
<223> OTHER INFORMATION: thrombin inhibitory peptide: hirudin 53-64

<400> SEQUENCE: 5

Cys Gly Ala Gly Ala Gly Asn Gly Asp Phe Glu Glu Ile Pro Glu Glu
1               5                   10                  15

Tyr Leu

```
<210> SEQ ID NO 6
<211> LENGTH: 6
<212> TYPE: PRT
<213> ORGANISM: Artificial Sequence
<220> FEATURE:
<223> OTHER INFORMATION: N-terminus of fibrin 414-427

<400> SEQUENCE: 6

Val Arg Pro Glu His Pro
1               5

<210> SEQ ID NO 7
<211> LENGTH: 15
<212> TYPE: PRT
<213> ORGANISM: Artificial Sequence
<220> FEATURE:
<223> OTHER INFORMATION: CEAK15 peptide

<400> SEQUENCE: 7

Cys Glu Ala Glu Ala Glu Ala Lys Ala Lys Ala Lys Ala Lys Cys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: CDAR15 peptide

<400> SEQUENCE: 8

Cys Asp Ala Asp Ala Asp Ala Asp Ala Arg Ala Arg Ala Arg Cys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: CDAR15 peptide

<400> SEQUENCE: 9

Cys Asp Asp Asp Asp Ala Ala Ala Ala Ala Arg Arg Arg Arg Cys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: CEAK15 peptide

<400> SEQUENCE: 10

Cys Glu Glu Glu Glu Ala Ala Ala Ala Ala Lys Lys Lys Lys Cys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: CDAR15 peptide

<400> SEQUENCE: 11

Cys Asp Asp Asp Asp Ala Ala Ala Ala Ala Arg Arg Arg Arg Cys
1               5                   10                  15
```

<210> SEQ ID NO 12
<211> LENGTH: 29
<212> TYPE: PRT
<213> ORGANISM: Artificial Sequence
<220> FEATURE:
<223> OTHER INFORMATION: dCoil-adIL29 dimeric coiled coil

<400> SEQUENCE: 12

Cys Leu Glu Ala Leu Glu Lys Lys Leu Ala Ala Leu Glu Cys Lys Leu
1               5                   10                  15

Gln Ala Leu Glu Lys Lys Leu Glu Ala Leu Glu Cys His
            20                  25

<210> SEQ ID NO 13
<211> LENGTH: 29
<212> TYPE: PRT
<213> ORGANISM: Artificial Sequence
<220> FEATURE:
<223> OTHER INFORMATION: dCoil-adLL29 dimeric coiled coil

<400> SEQUENCE: 13

Cys Leu Ala Asp Leu Glu Lys Arg Leu Asp Glu Leu Ala Cys Lys Leu
1               5                   10                  15

Glu Asp Ala Ala Lys Arg Leu Gln Ser Leu Ala Cys Lys
            20                  25

<210> SEQ ID NO 14
<211> LENGTH: 29
<212> TYPE: PRT
<213> ORGANISM: Artificial Sequence
<220> FEATURE:
<223> OTHER INFORMATION: dCoil-LA29 dimeric coiled coil

<400> SEQUENCE: 14

Cys Leu Ala Ala Leu Glu Ala Arg Leu Ala Ala Leu Glu Cys Arg Leu
1               5                   10                  15

Ala Ala Leu Glu Ala Arg Leu Ala Ala Leu Glu Cys Arg
            20                  25

<210> SEQ ID NO 15
<211> LENGTH: 29
<212> TYPE: PRT
<213> ORGANISM: Artificial Sequence
<220> FEATURE:
<223> OTHER INFORMATION: tCoil-LL29 trimeric bundle

<400> SEQUENCE: 15

Cys Leu Glu Ala Leu Glu Lys Lys Leu Ala Ala Leu Glu Cys Lys Leu
1               5                   10                  15

Gln Ala Leu Glu Lys Lys Leu Glu Ala Leu Glu Cys His
            20                  25

<210> SEQ ID NO 16
<211> LENGTH: 29
<212> TYPE: PRT
<213> ORGANISM: Artificial Sequence
<220> FEATURE:
<223> OTHER INFORMATION: tCoil-adII29 trimeric bundle

SEQUENCE: 16

Cys Ile Lys Gln Ile Glu Asp Lys Ile Glu Glu Ile Leu Cys Arg Ile
1               5                   10                  15

Tyr His Ile Glu Asn Glu Ile Ala Arg Ile Lys Cys Lys
            20                  25

<210> SEQ ID NO 17
<211> LENGTH: 29
<212> TYPE: PRT
<213> ORGANISM: Artificial Sequence
<220> FEATURE:
<223> OTHER INFORMATION: tCoil-IQN29 trimeric bundle

<400> SEQUENCE: 17

Cys Met Lys Gln Ile Glu Asp Lys Ile Glu Glu Ile Glu Cys Lys Gln
1               5                  10                  15

Lys Lys Ile Glu Asn Glu Ile Ala Arg Ile Lys Cys Lys
            20                  25

<210> SEQ ID NO 18
<211> LENGTH: 29
<212> TYPE: PRT
<213> ORGANISM: Artificial Sequence
<220> FEATURE:
<223> OTHER INFORMATION: tCoil-IQI129 trimeric bundle

<400> SEQUENCE: 18

Cys Met Lys Gln Ile Glu Asp Lys Ile Glu Glu Ile Leu Cys Lys Gln
1               5                  10                  15

Tyr His Ile Glu Asn Glu Ile Ala Arg Ile Lys Cys Lys
            20                  25

<210> SEQ ID NO 19
<211> LENGTH: 29
<212> TYPE: PRT
<213> ORGANISM: Artificial Sequence
<220> FEATURE:
<223> OTHER INFORMATION: qCoil-adLI20 trimeric bundle

<400> SEQUENCE: 19

Cys Leu Lys Gln Ile Glu Asp Lys Leu Glu Glu Ile Leu Cys Lys Leu
1               5                  10                  15

Tyr His Ile Glu Asn Glu Leu Ala Arg Ile Lys Leu Cys
            20                  25

<210> SEQ ID NO 20
<211> LENGTH: 24
<212> TYPE: PRT
<213> ORGANISM: Artificial Sequence
<220> FEATURE:
<223> OTHER INFORMATION: PXY24 peptide

<400> SEQUENCE: 20

Cys Pro Pro Gly Pro Pro Gly Pro Cys Gly Pro Pro Gly Pro Pro Gly
1               5                  10                  15

Cys Gly Pro Pro Gly Pro Pro Cys
            20

<210> SEQ ID NO 21
<211> LENGTH: 34
<212> TYPE: PRT
<213> ORGANISM: Artificial Sequence
<220> FEATURE:
<223> OTHER INFORMATION: PXY34 peptide

```
-continued

<400> SEQUENCE: 21

Cys Pro Pro Gly Pro Pro Gly Pro Cys Gly Pro Pro Gly Pro Pro Gly
1               5                   10                  15

Cys Gly Pro Pro Gly Pro Pro Cys Gly Pro Pro Gly Pro Pro Gly Pro
            20                  25                  30

Pro Cys
```